(12) United States Patent
Ono et al.

(10) Patent No.: US 6,332,683 B1
(45) Date of Patent: Dec. 25, 2001

(54) FUNDUS EXAMINATION APPARATUS

(75) Inventors: Shigeaki Ono, Utsunomiya; Shinya Tanaka; Toshiaki Okumura, both of Tokyo, all of (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/689,780

(22) Filed: Oct. 13, 2000

(30) Foreign Application Priority Data

| Oct. 15, 1999 | (JP) | 11-294525 |
| Oct. 15, 1999 | (JP) | 11-294526 |
| Jan. 12, 2000 | (JP) | 2000-003734 |

(51) Int. Cl.[7] ......................................... A61B 3/14
(52) U.S. Cl. ............................................. 351/210
(58) Field of Search .................... 351/205, 206, 351/207, 208, 209, 210, 211, 220, 221, 246

(56) References Cited

U.S. PATENT DOCUMENTS

| 4,856,891 | * | 8/1989 | Pflibsen et al. | 351/210 |
| 4,951,670 | | 8/1990 | Tanaka et al. | 128/648 |
| 5,031,623 | | 7/1991 | Kohayakawa et al. | 128/648 |
| 5,106,184 | | 4/1992 | Milbocker | 351/221 |
| 5,107,851 | | 4/1992 | Yano et al. | 128/648 |
| 5,270,749 | | 12/1993 | Okumura | 351/211 |
| 5,455,644 | | 10/1995 | Yazawa et al. | 351/206 |
| 5,500,696 | | 3/1996 | Masuda et al. | 351/205 |
| 5,615,683 | | 4/1997 | Toge et al. | 128/666 |
| 5,751,396 | | 5/1998 | Masuda et al. | 351/221 |
| 5,894,337 | | 4/1999 | Okinishi et al. | 351/205 |
| 5,976,096 | | 11/1999 | Shimizu et al. | 600/504 |
| 6,192,269 | | 2/2001 | Okumura et al. | 600/504 |
| 6,193,372 | * | 2/2001 | Okumura et al. | 351/221 |

FOREIGN PATENT DOCUMENTS

| 7-155299 | 6/1995 | (JP) . |
| 10-75931 | 3/1998 | (JP) . |

OTHER PUBLICATIONS

"Retinal laser Doppler velocimetry: toward its computer–assisted clinical use", B. L. Petrig, et al, Applied Optics, vol. 27, No. 6, Mar. 15, 1988.

* cited by examiner

*Primary Examiner*—George Manuel
(74) *Attorney, Agent, or Firm*—Fitzpatrick, Cella, Harper & Scinto

(57) ABSTRACT

Fundus examination is effected by the steps of irradiating the fundus of an examined eye with a measuring beam through a deflector, irradiating the fundus of the eye with a tracking beam through the deflector to thereby obtain tracking information, and controlling the deflector on the basis of the tracking information and executing tracking, calculating a position at which the reliability of a signal obtained by a light receiving system is relatively improved during the tracking, and controlling the deflector so that the measuring beam may be irradiated to this position; and frequency-analyzing the signal obtained by the light receiving system and calculating the velocity of blood flow. The aforementioned reliability is evaluated by means of the SN ratio and quality value of the signal.

16 Claims, 15 Drawing Sheets

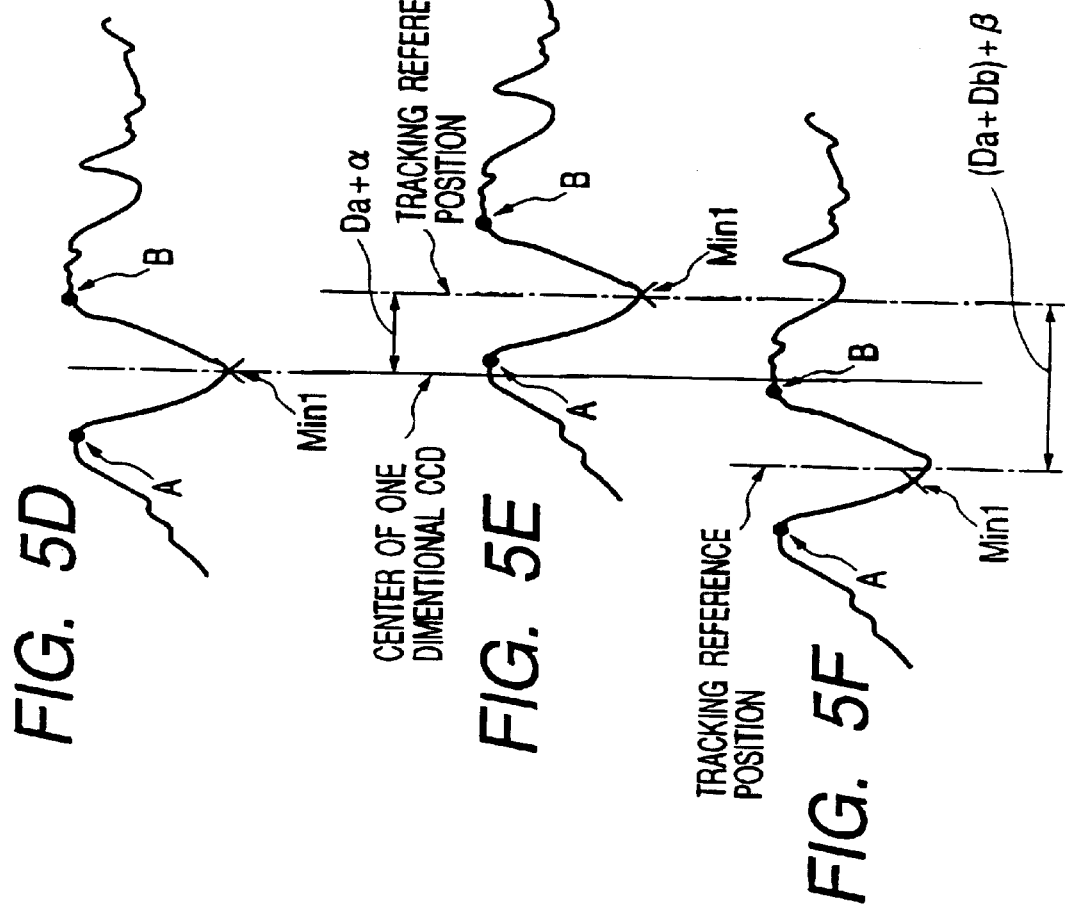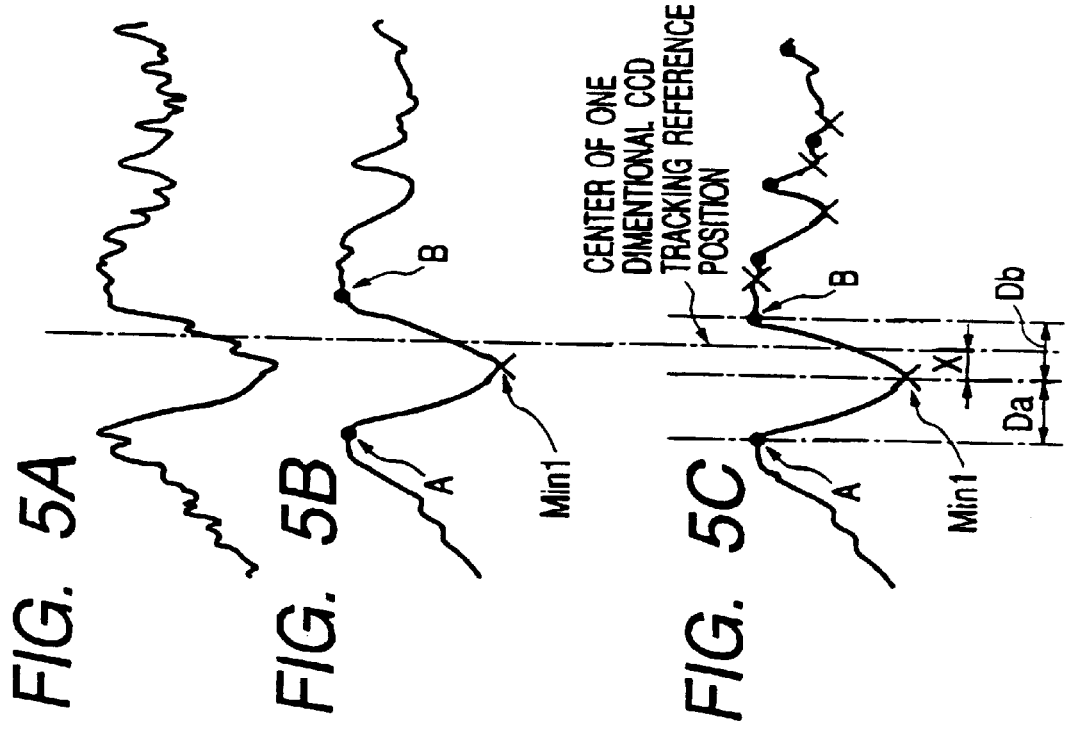

FLOW RATE DISTRIBUTION

FUNDUS EXAMINATION APPARATUS

BACKGROUND OP THE INVENTION

Field of the Invention

This invention relates to a fundus examination apparatus such as a laser-Doppler-type, blood-flow meter for measuring the velocity of blood flow in a vessel on the fundus. Further, this invention covers a flow meter for measuring the flow velocities of various fluids.

There is a laser-Doppler, fundus-blood-flow meter as the application of a flow meter. This device irradiates a vessel to be measured of the fundus of an examined eye with a laser beam of a wavelength $\lambda$, receives the scattered light thereof with a photodetector, detects the interference signal of a Doppler-shifted component of scattered, reflected light from blood cells and scattered light from a stationary vesselcular wall, frequency-analyzes it, and finds the velocity of the blood flow.

Assuming that the scattering intensity of the blood flow in a vessel as the object is proportional to the number of blood cells and that the distribution of the cell density is uniform and the flow thereof is the Poiseuille flow, it is derived that the spectral density of the Doppler shift obtained becomes a flat spectral distribution up to a cut-off frequency $\Delta fmax$ corresponding to the maximum flow velocity at the center of the vessel. In the laser Doppler type fundus blood flow meter, this $\Delta fmax$ is detected as a physical amount proportional to the maximum flow velocity.

In the bi-directional observation method this cut-off frequency $\Delta fmax$ is found relative to signals received from two different directions, whereby the relation between $\Delta fmax$ and Vmax is expressed by the angle $\Delta \alpha$ formed between two observation directions determined by the construction of the apparatus and the length of the eye axis and the magnitude of the wave number vector k, i.e., $2\pi/\lambda$ as shown by the following expression:

$$Vmax=\{\lambda/(n-\alpha)\}\cdot|\Delta fmax1-\Delta fmax2|/\cos \delta, \quad (1)$$

where $\Delta fmax1$ and $\Delta fmax2$ are the maximum shifts of the frequencies calculated from the received signals received by two light receivers, $\lambda$ is the wavelength of the laser beam, n is the refractive index of the measured region, $\alpha$ is the angle formed between two light receiving optical axes in the eye, and $\beta$ is the angle formed between a plane defined by the two light receiving optical axes in the eye and the blood flow velocity vector. By effecting measurement from two directions as described above, the contribution of the incidence direction of the measuring beam is offset, and the blood flow in any region on the fundus of the eye can be measured. Also, by making the angle $\beta$ formed between the line of intersection between the plane defined by the two light receiving optical axes and the fundus of the eye and the blood-flow-velocity vector coincident, $\beta=0°$ and the true maximum blood flow velocity can be measured.

When the vesselcular shape and blood-flow velocity of a particular region of the vessel in the fundus of the eye are to be measured, it is necessary for the measuring beam to be accurately positioned onto the target vessel within the measuring time. But actually there are micro eye movements. Therefore, it is difficult to continue to accurately keep the measuring beam onto the target vessel. In order to solve this problem in, the auto-tracking technique of detecting the vesselcular position and moving the position of the measuring beam onto the target vessel in real time corresponding to the micro eye movements is disclosed in Japanese Patent Application Laid-Open No. 6-503733 and Japanese Patent Application Laid-Open No. 7-155299. In these documents, there is adopted a method of irradiating the fundus with a tracking beam from an illuminating light source in a tracking beam optical system and the measuring beam through the intermediary of a rotating mirror at a rotating position, and the design of the device is made such that the spot of the measuring beam irradiates the conjugate point on the fundus of the eye of a tracking reference position on a tracking sensor. The vessel is illuminated by the tracking beam and the image thereof is enlarged and projected onto the tracking sensor, and the rotating mirror is moved so that this vesselcular image may come to the tracking reference position, whereby the measuring beam always continues to irradiate a predetermined vessel.

However, there will be no problem if the tracking-reference-position conjugate point and the measuring beam spot are coincident with each other. But if the tracking-reference-position conjugate point and the measuring beam spot do not coincide with each other due to the structure of the apparatus and the principle of measurement, for example, for the reason that the measuring beam irradiates the fundus at a plurality of different angles, the incidence positions of the tracking beam and the measuring beam differ from each other at the corneal position of the examined eye, and the center of the tracking beam on the vessel and the measuring beam are not coincident with each other.

Further, when there is present great corneal astigmatism or the like, deviation occurs between the center of the tracking beam on the vessel and the measuring beam, and accurate measurement becomes impossible in spite of the tracking system that is operating. In order to solve this problem, an apparatus having correcting means capable of suitably resetting the deviation distance between the center of the tracking beam on the vessel and the measuring beam is disclosed in Japanese Patent Application Laid-Open No. 10-075931. In this example, however, an operator must correct the deviation distance between the center of the tracking beam on the vessel and the measuring beam by visual confirmation and a manual technique and therefore, there is the point to be improved that the correction is greatly affected by not only the operator's skill but the instability of a fixed eye due to conditions such as the operator being sick or advanced in years.

Now, it has heretofore been the ordinary practice to determine each cut-off frequency $\Delta fmax$ by the visual judgeluent of the operator. As an improvement over this, there is the technique described in APPLIED OPTICS, vol. 27, No. 6, pp. 1126 to 1134 (1988), "Retinal laser Doppler velocimetry toward its computer-assisted clinical use" (B. L. Petrig, C. E. Riva). Although there is no specific description in this, it is inferred that the cut-off frequency $\Delta fmax$ is found by considering an ideal model in which the power spectrum of an FFT waveform vertically falls at the cut-off frequency $\Delta fmax$. The accuracy of this determination of the cut-off frequency increases as the result of frequency analysis approximates the ideal model. That is, the degree of reliability of the measured value can be represented by evaluating the difference from the ideal model. In the above document, after the determination of the cut-off frequency, this difference from the ideal model is evaluated by the use of that cut-off frequency $\Delta fmax$ and is regarded as the degree of reliability of measurement.

In the above-described evaluation method, however, it is difficult to obtain a result in a moment because the amount of calculation for determining the final cut-off frequency is vast. Accordingly, when for example, the confirmation of a set measuring condition such as the position of the measuring beam relative to the vessel is to be determined in advance by the quality of a tentatively acquired measurement signal, much calculation time is taken and therefore it is difficult to judge the quality of the condition setting in real time. Further, when use is made of an evaluation method of judging the quality of ti he signal from the shape of its spectrum, if the intensity of the signal component of a Doppler signal is not sufficiently large, the correct measured value from that signal is not provided, shape comparison is not correctly conducted, and the signal is judged to be very good.

SUMMARY OF THE INVENTION

It is a primary object of the present invention to provide an apparatus and a method improved over the above-described example of the prior art. It is a more specific-object of the present invention to provide a technique that can automatically irradiate a blood vessel to be measured with a measuring beam in the vicinity of the best position of a measured vessel. It is a further more specific object of the present invention to provide a technique that can determine the S/N ratio of a measurement signal within a short time and accurately discriminate the quality thereof.

A fundus examination apparatus according to the present invention for achieving the above objects comprises:

an irradiating system for irradiating the fundus of an examined eye with a measuring beam, the irradiating system including a deflector for deflecting the measuring beam and being capable of changing the irradiated position of the measuring beam;

a light receiving system for receiving the scattered light from the fundus of the eye by the measuring beam, and obtaining a signal necessary for examination;

a tracking system for irradiating the fundus of the eye with a tracking beam through the deflector, and controlling the deflector on the basis of the image signal of a region illuminated by the tracking beam; and a controller having a processor for evaluating the signal obtained by the light receiving system, and controlling the deflector on the basis thereof during the execution of tracking to thereby correct the irradiated position of the measuring beam.

Also, a fundus examination apparatus according to the present invention for achieving the above objects comprises:

an irradiating system for irradiating the fundus of an examined eye with a measuring beam;

a light receiving system for receiving the scattered light from the fundus of the eye by the measuring beam, and obtaining a signal necessary for examination; and a processor for frequency-analyzing the signal obtained by the light receiving system, and calculating the velocity of blood flow in the vessel on the fundus of the eye;

the processor executing signal processing including a first step of calculating an integrated curve in which the spectral distribution of the result of the frequency analysis is accumulated from a high frequency side, and a second step of dividing the spectral distribution into at least two areas that are a noise area existing in a high frequency area and approximated to white noise, and a signal area existing more adjacent to a low frequency side than the noise area, by the use of the integrated curve.

Further objects and preferred forms of the present invention will become apparent from the following description of some embodiments of the invention.

BRIEF DESCRIPTION OF THE DRAWINGS

FIGS. 5A, 5B, 5C, 5D, 5E and 5F are illustrations of a vesselcular image signal waveform.

DESCRIPTION OF THE PREFERRED EMBODIMENTS

The present invention will hereinafter be described with a fundus blood flow meter for measuring the velocity of a blood flow flowing through a vessel on the fundus of an examinee's eye, taken as an example of a fundus examination apparatus. The present invention is applicable not only to the examination of the blood flow, but also to the examination of the fundus of the eye. Also, the present invention can be directed to the examination of vessels not only on the fundus of the eye but also on various regions. Further the present invention can be applied to a flow meter for measuring the flow velocity of fluids such as liquid and gases.

Embodiment

Figure 1:
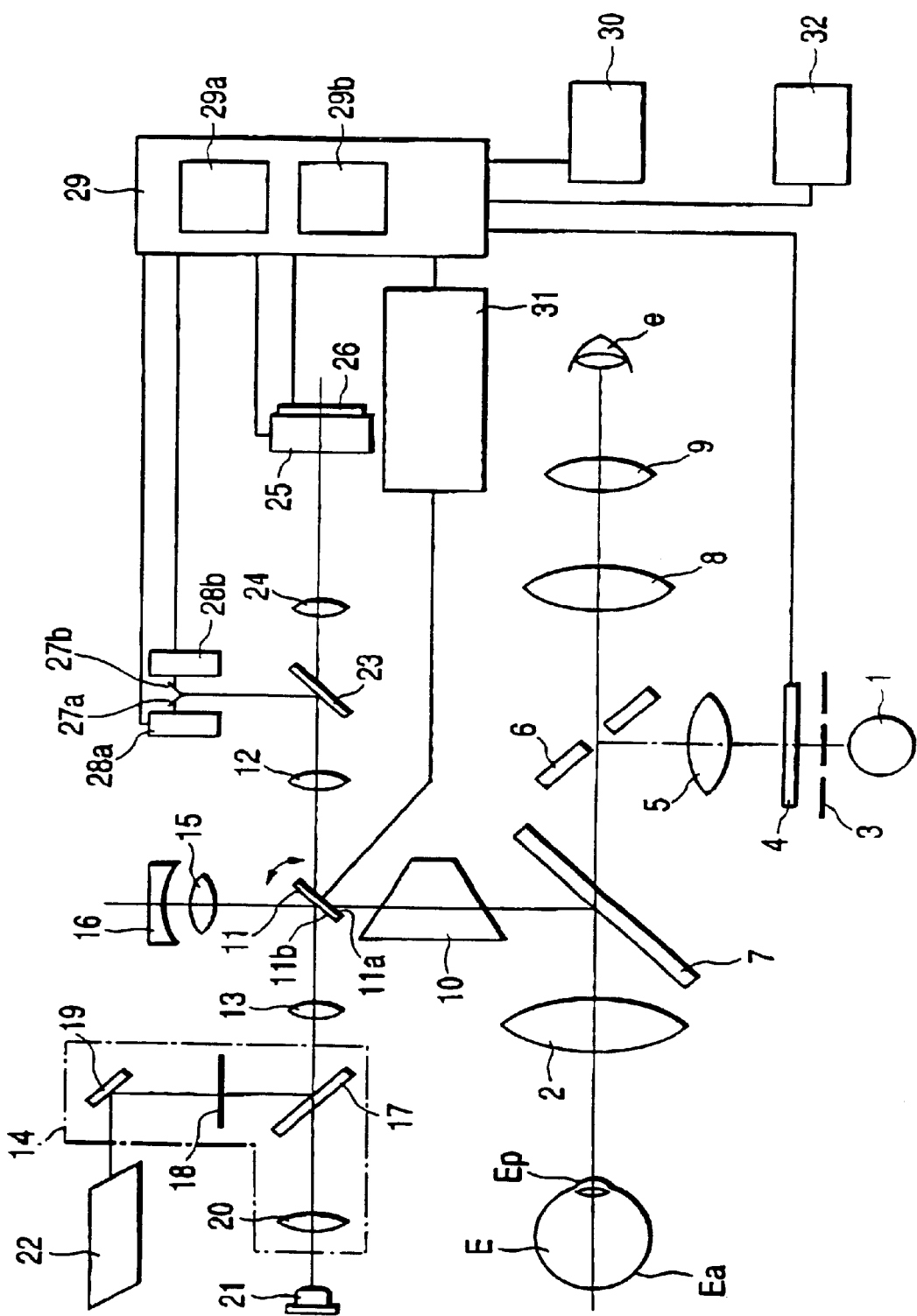
FIG. 1 shows the construction of a fundus blood flow meter according to a first embodiment of the present invention.

FIG. 1 shows the construction of a laser Doppler type fundus blood flow meter according to an embodiment of the present invention. On an illuminating optical path leading from an observation light source 1 comprising a tungsten lamp or the like emitting white light to an objective lens 2 opposed to an examined eye E, there are successively arranged a ring slit 3, a transmission type liquid crystal plate 4, which is a fixed eye mark displaying element disposed at a position optically conjugate with the fundus Ea of the examined eye E and movable along the optical path, a relay lens 5, an apertured mirror 6, and a band-pass mirror 7 transmitting wavelength light in the yellow range and reflecting almost all of the other light beams, whereby a fixed eye-target-projection optical system is constituted. A fundus observation optical system is constructed on the optical path behind the apertured mirror 6, and an imaging lens 8 and an eyepiece 9 movable along the optical path are arranged and lead to an operator's eye e.

On the optical path in the reflecting direction of the band-pass mirror 7, there are arranged an image rotator 10 and a galvanometric mirror (deflector) 11 having a rotary shaft perpendicular to the plane of the drawing sheet of FIG. 1 and a cut-away portion below the rotary shaft and having both its surfaces polished. A relay lens 12 movable along the optical path is disposed in the reflecting direction of the lower reflecting surface 11a of this galvanometric mirror 11. A lens 13 whose front side focal plane is in conjugate relationship with the pupil Ep of the examined eye E, and a focusing unit 14, movable along the optical path, are disposed in the reflecting direction of the upper reflecting surface 11b of the galvanometric mirror 11, and the galvanometric mirror 11 is disposed on the focal plane of the lens 13. A lens 15 and a concave mirror 16 are disposed rearwardly of the galvanometric mirror 11, and there is structured a relay optical system for directing a light beam not reflected by the lower reflecting surface 11a of the galvanometric mirror 11 but passing trough the cut-away portion to the upper reflecting surface 11b of the galvanometric mirror 11.

In the focusing unit 14, a dichroic mirror 17 is disposed on the same optical path as the lens 13, a mask plate 18 having a rectangular stop for forming a tracking index and a mirror 19 are arranged on the optical path in the reflecting direction of the dichroic mirror 17, a lens 20' is disposed on the optical path in the transmitting direction of the dichroic minor 17, and the focusing unit 14 is made movable as a unit.

Also, on the optical path in the incidence direction of the lens 20, there is disposed a measuring light source 21, such as a laser diode emitting, for example, collimated coherent red light. Further, on the optical path in the incidence direction of the mirror 19, there is disposed a tracking light source 22, such as a helium neon laser emitting, for example, green light of high luminance differing from the other light sources.

Behind the relay lens 12, there are successively arranged a dichroic mirror 23, a magnifying lens 24, an image intensifier 25 and a one-dimensional CCD 26, whereby a vesselcular detecting system is constituted. In the reflecting direction of the dichroic mirror 23, there are arranged a pair of mirrors 27a and 27b and a pair of photomultipliers 28a and 28b, whereby a measuring light receiving optical system is constituted. While for the convenience of illustration, all the optical paths have been shown on the same plane, the reflecting direction of the dichroic mirror 23 is orthogonal to the plane of the drawing sheet of FIG. 1.

It is a system controller 29 that controls the system of the entire apparatus, and this contains therein a processor 29a for carrying out various kinds of calculating processes which will be described later, and a memory 29b connected thereto. The system controller 29 has connected thereto the outputs of the image intensifier 25, the one-dimensional CCD 26, the photomultipliers 28a, 28b and an input device 30 operated by the operator. Also, the output of the system controller 29 is connected to a control driving circuit 31 for controlling and driving the galvano-metric mirror 11, and a display 32 for displaying the result of the measurement. Also, the transmission type liquid crystal plate 4, the imaging lens 9, the relay lens 12 and the focusing unit 14 are adapted to be moved in the direction of the optical axis in operative association with one another by the operator operating a focusing knob (not shown) so that the transmission type liquid crystal plate 4, the fundus of the operator's eye e, the mask plate 18 and the light receiving surface of the image intensifier 25 may always be optically conjugate with the fundus Ea of the examined eye E.

Figure 2:
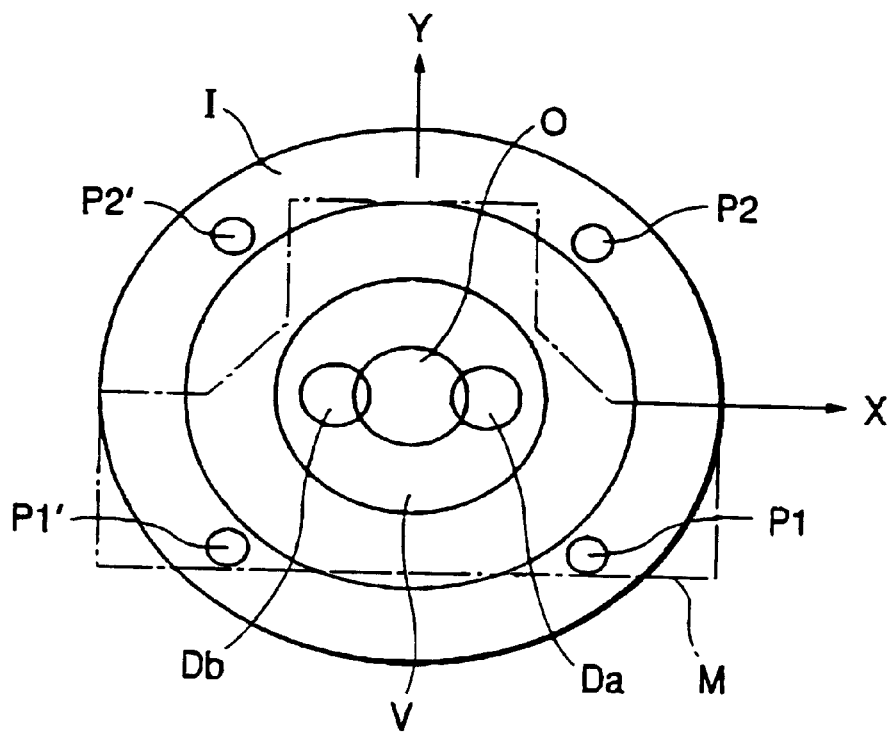
FIG. 2 is an illustration of each light beam on a pupil plane.

FIG. 2 shows the disposition of a beam on the pupil Ep of the examined eye E, and in FIG. 2, the letter I designates the image of the ring slit 3 and an area illuminated by yellow illuminating light, the letter O denotes the image of the opening portion of the apertured mirror 6 formed by a fundus observation beam, the letter V designates the image of the effective portions of the upper and lower reflecting surfaces 11a and 11b of the galvanometric mirror 11, which are provided by a vesselcular received beam, and the letters Da and Db denote the images of the pair of mirrors 27a and 27b, which are provided by two measuring received beams. Also, P1, P1', P2 and P2' designate the incidence positions of the beams on the galvanometric mirror 11, and an area M indicated by a dot-and-dash line is the image of the lower reflecting surface 11a of the galvanometric mirror 11.

Figure 3:
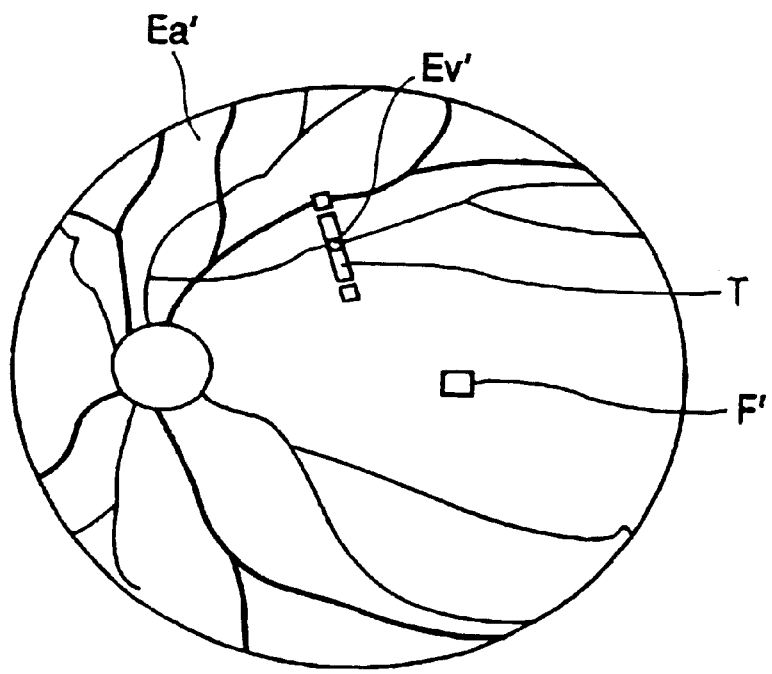
FIG. 3 is an illustration of an observed fundus image.

White light emitted from the observation light source 1 passes through the ring slit 3, illuminates the transmission type liquid crystal plate 4 from its back, passes through the relay lens 5, and is reflected by the apertured mirror 6. Only the light of the wavelength in the yellow range is transmitted through the band-pass mirror 7, passes through the objective lens 2, and is once imaged as a fundus illuminating beam image 1 on the pupil Ep of the examined eye E, and thereafter substantially uniformly illuminates the fundus Ea of the eye. At this time, a fixed eye mark F is displayed on the transmission type liquid crystal plate 4. This fixed eye mark F is projected onto the fundus Ea of the examined eye E by illuminating light, and is presented as a fixed eye mark image F' to the examinee, as shown in FIG. 3.

The reflected light from the fundus Ea of the eye returns along the same optical path, is taken out as a fundus observation beam image O from on the pupil Ep, and passes through the objective lens 2, the band-pass mirror 7, the central opening portion of the apertured mirror 6, the imaging lens 8 and the eyepiece 9. As a result, the fundus image Ea' as shown in FIG. 3 becomes observable by the operator's eye e and therefore, the alignment of the apparatus is effected while this fundus image Ea' is observed through the eyepiece 9.

A measuring beam emitted from the measuring light source 21 and collimated passes through the lens 20 and is transmitted through the dichroic mirror 17. On the other hand, a tracking beam emitted from the tracking light source 22 is reflected by the mirror 19, and is shaped into a desired shape by the mask plate 18, whereafter it is reflected by the dichroic mirror 17 and is superposed on the measuring beam being imaged into a spot shape at a position conjugate with the center of the opening portion of the mask 18 by the lens 20. The measuring beam and the tracking beam superposed thereon pass through the lens 13, are reflected by the upper reflecting surface 11b of the galvanometric mirror 11, pass through the lens 15, and thereafter are reflected by the concave mirror 16, again passes through the lens 15 and are returned toward the galvanometric mirror 11.

Since the galvanometric mirror 11 is disposed at a position conjugate with the pupil Ep of the examined eye E, the image thereof is of a shape indicated by the dot-and-dash line M of FIG. 2 on the pupil Ep. Further the lens 15 and the concave mirror 16 are disposed concentrically with each other on the optical axis, and cooperate with each other to be given the function of a relay optical system for imaging the galvanometric mirror 11 at −1 time. Accordingly, the beams reflected at the positions P1 and P1' on the image M of the galvanometric mirror 11 are returned to the positions P2 and P2', respectively, on the cut-away portion of the galvanometric mirror 11. As the result, the beams travel toward the image rotator 10 without being reflected by the galvanometric mirror 11.

These two beams are deflected by the band-pass mirror 7 via the image rotator 10, and irradiate the fundus Ea of the examined eye E through the objective lens 2. Thus, the measuring beam and the tracking beam are reflected in the upper reflecting surface 11b of the galvanometric mirror 11, are again returned, and come into the galvanometric mirror 11 in a state in which they are eccentric from the optical axis of the objective lens 2, and are imaged as spot images P2 and P2' on the pupil Ep as shown in FIG. 2, whereafter they irradiate the fundus Ea of the eye in a spot shape.

The scattered reflected lights of the measuring beam and the tracking beam from the fundus Ea of the eye are again condensed by the objective lens 2 and almost all of the beams are reflected by the band-pass mirror 7, pass through the image rotator 10, are reflected by the lower reflecting surface 11a of the galvanometric mirror 11, and pass through the relay lens 12, and the measuring beam and the tracking beam are separated from each other in the dichroic mirror 23.

The tracking beam is transmitted through the dichroic mirror 23, and is imaged on the photoelectric surface of the image intensifier 25 as a vesselcular image Ev' magnified more than the fundus image Ea' by the fundus observation optical system by the magnifying lens 24, and is amplified and thereafter is image picked up by the one-dimensional CCD 26. Then, on the basis of the vesselcular image Ev' picked up by the one-dimensional CCD 26, data representative of the amount of movement of the vesselcular image Ev' is prepared in the system controller 29, and the amount of movement of the vesselcular image Ev' is outputted to the control driving circuit 31. The control driving circuit 31 drives the galvanometric mirror 11 so as to compensate for this amount of movement, thereby effecting the tracking of the vessel at the portion to be measured.

Also, the measuring beam is reflected by the dichroic mirror 23, is further reflected by the pair of mirrors 27a and 27b, and is received by the photomultipliers 28a and 28b. The outputs of these photomultipliers 28a and 28b are outputted to the system controller 29, this light reception signal is frequency-analyzed, and the velocity of blood flow in the fundus Ea of the eye is found.

On the other hand, of the scattered reflected lights of the measuring beam and the tracking beam from the fundus Ea of the eye condensed by the objective lens 2, some beam transmitted through the band-pass mirror 7, like the reflected scattered light from the fundus Ea of the eye of the beam emitted from the observation light source 1, passes through the opening portion of the apertured mirror 6, the imaging lens 8 and the eyepiece 9 to the operator's eye e, and as shown in FIG. 3, a tracking eye mark image T and the fixed eye mark image F' become observable by the operator with an observation fundus image Ea'.

In case of measurement the operator first operates an operating rod, not shown, to thereby perform alignment so that the optical axis of the examined eye E and the optical axis of the objective lens 2 may coincide with each other. Next, the operator operates a focusing knob while observing the fundus image Ea' to thereby focus on the fundus Ea of the examined eye E. As a result, the fixed eye mark F on the transmission type liquid crystal plate 4 and the fundus Ea of the eye become optically conjugate with each other and the fixed eye mark F is presented to the examined eye E. When the examinee fixes his eyes on the fixed eye mark image F', the operator can observe the fundus image Ea' as shown in FIG. 3. The operator then operates the input device 30, moves the fixed eye mark F, and induces the examined eye E to move so that the measured region may come into the vicinity of substantially the center of the observation field of view.

The operator further operates the input device 30 to thereby irradiate the fundus Ea of the eye with the tracking beam, operates a rotator operating knob, not shown, so that as shown in FIG. 3, the tracking eye mark T and the measured vessel may become perpendicular to each other, and controls the angle of the galvanometric mirror 11 so that the measuring beam may irradiate the measured vessel.

The vessel Ev irradiated by the tracking bean is formed as the vesselcular image Ev' on the photoelectric surface of the image intensifier 25, and is amplified, and thereafter is image-picked up on the one-dimensional CCD 26, and is inputted as an image signal to the system controller 29. The operator determines the measured region, and thereafter operates the input device 30 again to thereby input the start of tracking.

Figure 4:
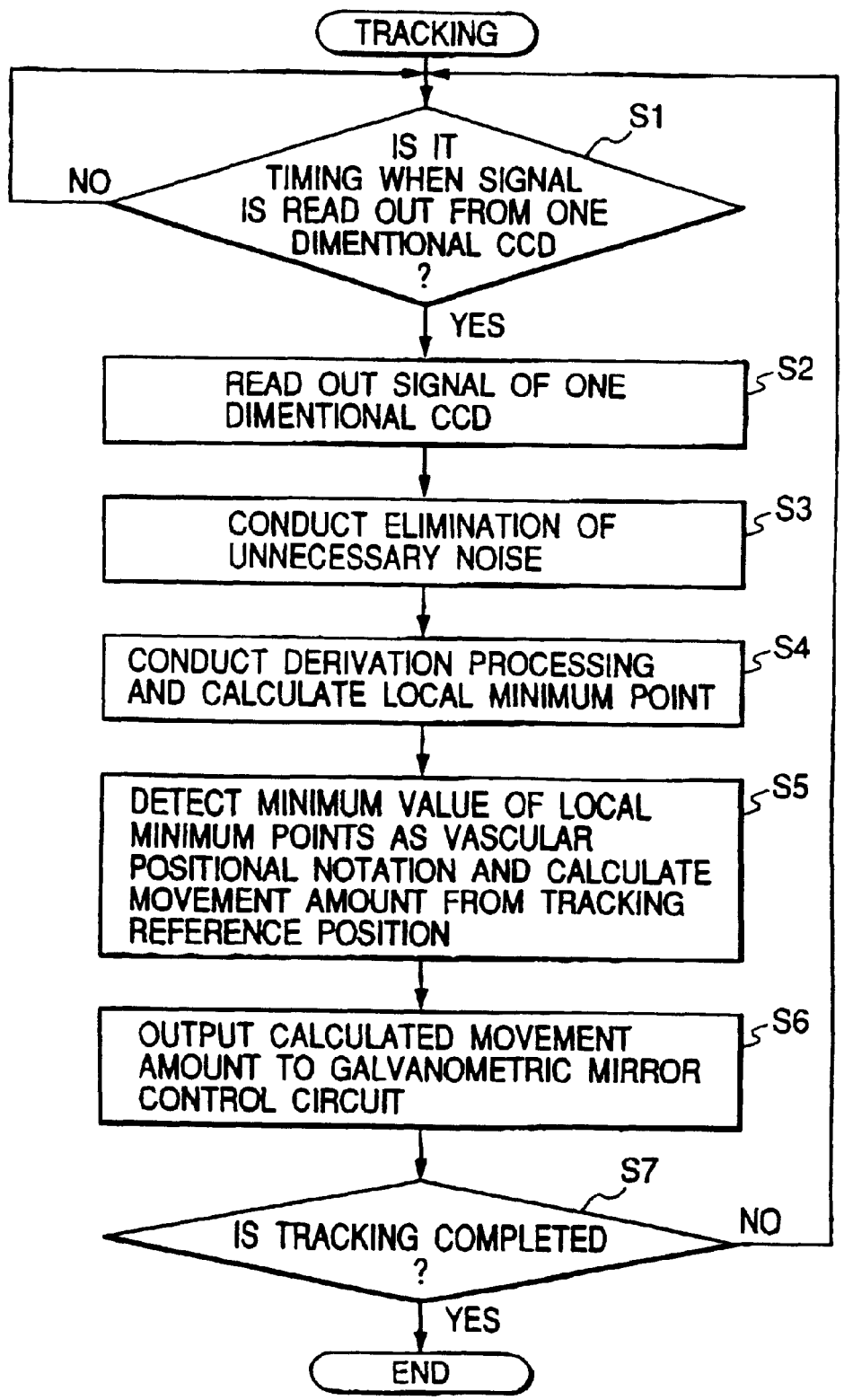
FIG. 4 is a flow chart of a tracking process.

FIG. 4 shows a flow chart of the tracking operation of the system controller 29. The vesselcular image Ev' picked up by the one-dimensional CCD 26 has its signal waveform as shown in FIG. 5A outputted to the system controller 29 after the lapse of a predetermined accumulation time, and the processor 29a, at a step S1, judges whether it is the timing when the signal is read out from the one-dimensional CCD 26. If it is the timing when the signal is read out, the processor 29a, at a step S2, reads out the signal of the one-dimensional CCD 26. In order to eliminate from this signal waveform any high frequency component noise unnecessary for the extraction of the characteristic point of the vesselcular image Ev', a filter process is conducted at step S3, and a signal waveform as shown in FIG. 5B is calculated. In order to calculate the position information of the vesselcular image Ev' from this signal waveform, the characteristic point of the vesselcular image is extracted.

First, at a step S4, derivation processing is conducted and a plurality of local minimum points are calculated. Next, at a step S5, a point of the plurality of local minimum points calculated at the step S4, which assumes a minimum value, e.g. Min1 shown in FIG. 5B, is detected. This point is substantially the central position of the vesselcular image Ev' and therefore, the movement amount x from the tracking reference position of the vesselcular image Ev' is calculated as the position information of the vesselcular image Ev', and at a step S6, the movement amount x is outputted to the galvanometric-mirror-control driving circuit 31, and the galvanometic-mirror-control driving circuit 31 drives the galvanometric mirror 11 so as to correct the movement amount x. Thereby, as shown in FIG. 5D, the tracking operation is performed substantially at the center of the vesselcular image Ev'. The system controller 29 repeats the operations of steps S1 to S7 until there is the input of the termination of tracking to the input device 25, and starts the automatic correcting operation for the irradiated position of the measuring beam when tracking is started.

Figure 6:
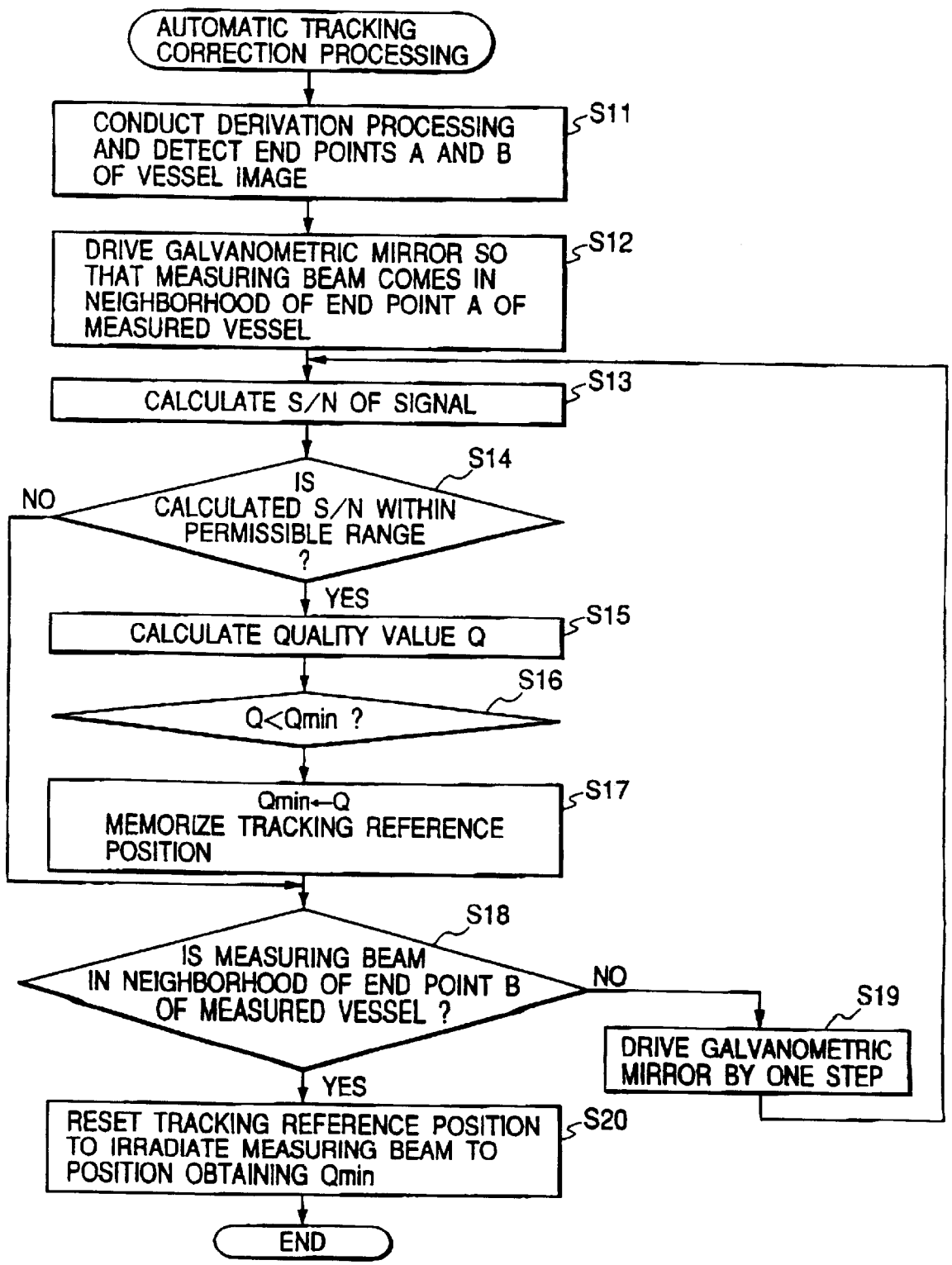
FIG. 6 is a flow chart of a system controlling process.

FIG. 6 shows a flow chart of the automatic correcting operation for the irradiated position of the measuring beam. First, at a step S11, the processor 29a of the system controller 29 conducts derivation processing to the signal waveform after suitable filter processing has been conducted at the step S3 of FIG. 4, and calculates the local maximum points and the local minimum points. The local maximum points and the local minimum points thus calculated are indicated by • and X, respectively, in the signal waveform of FIG. 5C. Further, the minimum value Min1 of the local minimum points and the local maximum points A and B nearest to the minimum value Min1 on the opposite sides of the minimum value Min1 are detected. These points A and B are the end points of the vesselcular image, and the space between the points A and B substantially represents the vesselcular image Ev'. Next, at a step S12, the distance Da between the point A and the minimum value Min1 and the distance Db between the point B and the minimum value Min1 are calculated, and as shown in FIG. 5E, the tracking reference position is rightwardly moved by Da +, and thereafter this value is outputted to the galvanometric-mirror-control driving circuit 31, which thus drives the galvanometric mirror 11.

Figure 7A:
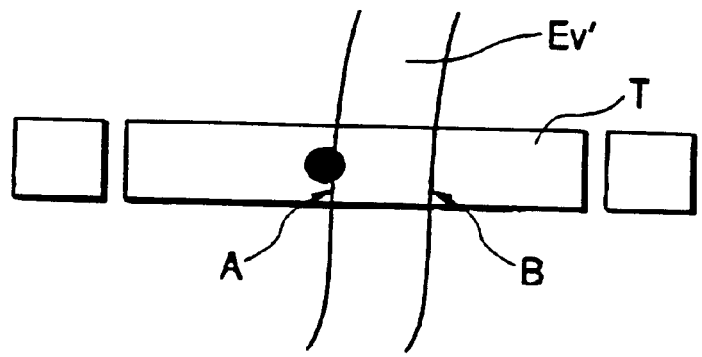
FIGS. 7A, 7B and 7C are illustrations of a tracking index image.
Figure 7B:
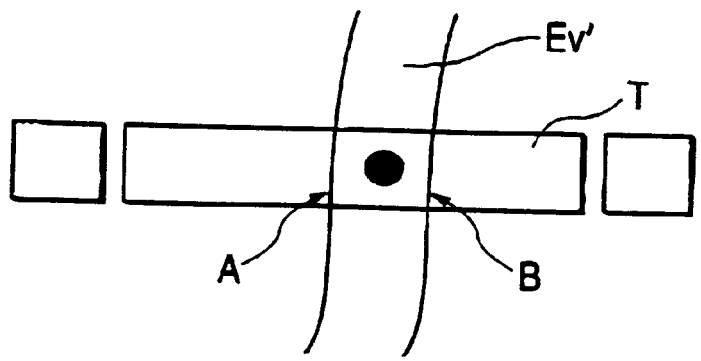
Figure 7C:
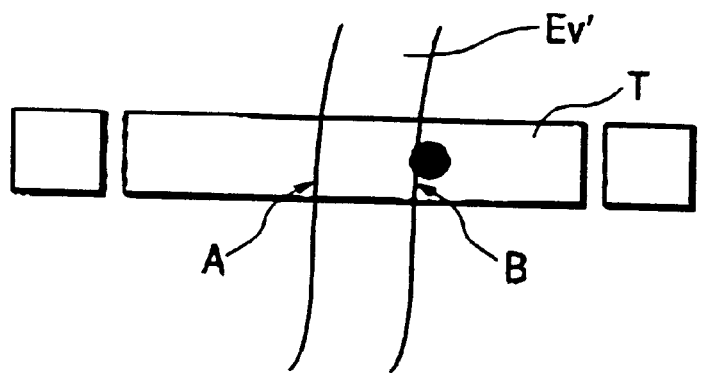

FIGS. 7A to 7C show enlarged views of a tracking index image T irradiated to the vesselcular image Ev', and in the place wherein the tracking reference position has been moved to a position shown in FIG. 5E, the measuring beam irradiates the eye substantially in the vicinity of the point A of the vesselcular image Ev', as shown in FIG. 7A. Further, at a step S13, the SN ratio of the measurement signal obtained from the photomultipliers 28a and 28b is calculated by a method that will be described later. If at a step S14, this SN ratio is within an allowable range, the quality value Q of the measurement signal obtained from the photomultipliers 28a and 28b is further calculated at a step S15 by a method to be described later, and whether the quality value Q is an optimum value is evaluated at a step S16. If the quality value Q at this time is the optimum value, at a step S17, the tracking reference position at this time is stored in the memory 29b connected to the processor 29a. For example, the optimum value of the quality value Q may be a minimum value Qmin.

Further, the steps S13 to S17 are each executed while the tracking reference position is moved leftward by a step until the tracking reference position, at which the movement distance shown in FIG. 5F becomes (Da+Db)+β, is reached. When the tracking reference position has been moved to the position shown in FIG. 5F, the irradiated position of the vesselcular image Ev' irradiated by the measuring beam becomes such as shown in FIG. 7C, and the measuring beam irradiates the eye substantially in the vicinity of the point B of the vesselcular image Ev'. The movement amount per step needs be set to a value so that which the quality value Q is changed in accordance with the movement of the irradiated position of the measuring beam, and in the present embodiment, it is set so as to be 2 μm on the fundus image Ea'.

Also, when for example, the measuring beam irradiates the eye at a plurality of different angles, even if the conjugate point of the tracking reference position and the measuring beam spot on the pupil conjugate mirror do not coincide with each other or even if great corneal astigmatism or the like is present in the examined eye E and the center of the tracking beam on the vessel and the measuring beam become in coincident with each other, the angle α of expression (1), formed between two light receiving optical axes in the eye, and the angle β, formed between a plane formed by the two light receiving optical axes in the eye and the velocity vector of blood flow, are set to such values that the measuring beam can sufficiently irradiate the vesselcular image Ev'.

In this manner, finally, such a position that the SN ratio of the measurement signal obtained by the photomultipliers 28a and 28b is within an allowable range, and the quality value Q of the measurement signal becomes the optimum value, which may be the minimum value Qmin, is detected, and at a step S20, a new tracking reference position is given to the galvanometric-mirror-control driving circuit 31 to thereby drive the galvanometric mirror 11 so that the measuring beam may irradiate this position, whereby the tracking operation centering around the new tracking reference position is performed. After tracking is then started, the operator operates the input device 25 to thereby input the start of measurement, whereupon measurement is started.

(a) Method of Calculating the Quality Value Q

Figure 8:
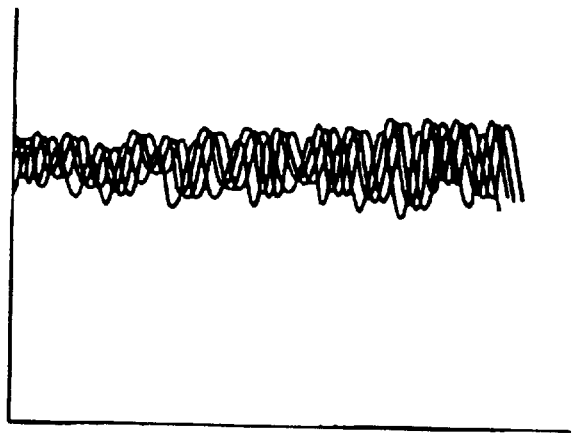
FIG. 8 is a graph of a Doppler shift measurement signal.
Figure 9:
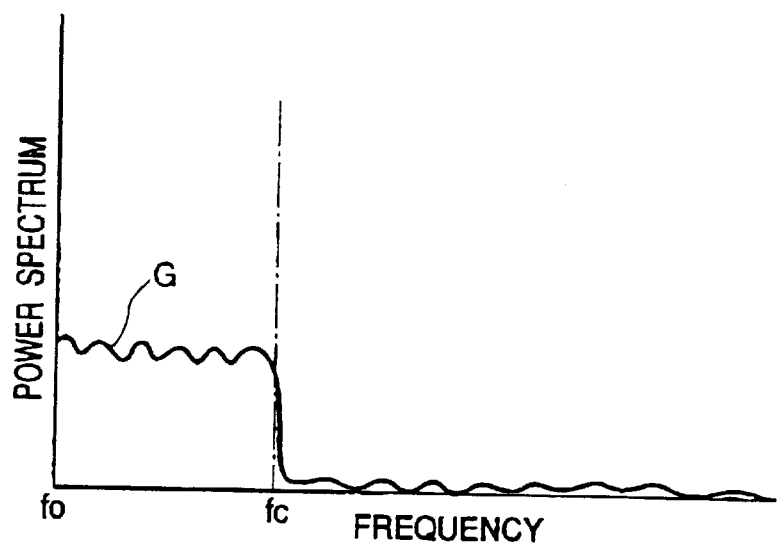
FIG. 9 is a graph of an FFT analysis line and the integrated line thereof.

FIG. 8 shows the primary signal of the blood flow state obtained by the use of the laser Doppler shift, and the ordinate axis represents the output and abscissa axis represents time. FIG. 9 is an FFT graph obtained by frequency analyzing the primary signal by using a fast Fourier transformation (FFT), and the ordinate axis represents output and the abscissa axis represents frequency, meaning velocity. A cut-off frequency fc, in which the output suddenly drops from a frequency area of a substantially constant output, is present in the FFT line G. This is a frequency corresponding to the highest velocity of the object area measured form the laser Doppler shift, and the system controller 29 analyzes this FFT line G and finds the cut-off frequency fc.

Figure 10:
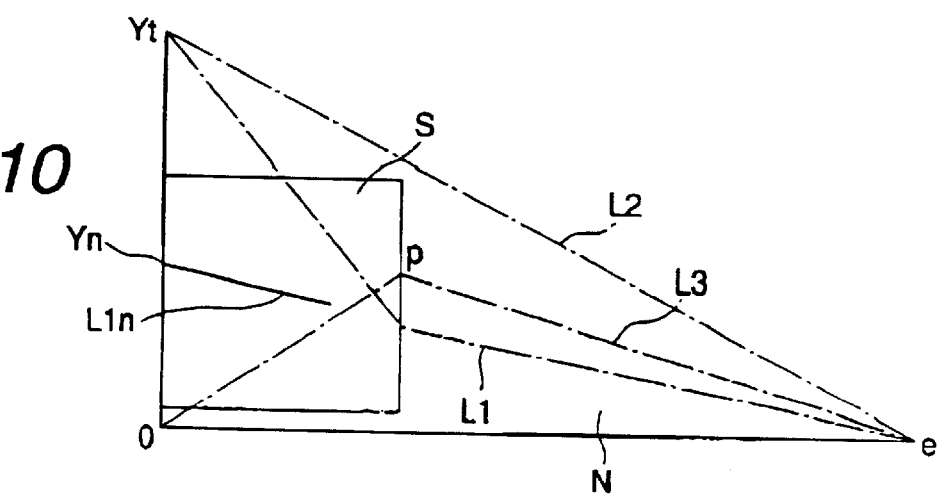
FIG. 10 is a graph of the theoretical shape of a light reception signal.

When the size of the light receiving pupil is neglected, the theoretically found shape of the FFT line can be divided into a signal portion S indicative of a Doppler shift and a white noise portion N on the high frequency side, as shown in FIG. 10. When this waveform is integrated from the high frequency side, there is obtained a polygonal line indicated by L1 from the maximum value p, and a value obtained by subtracting L1 from a straight line L2 linking the starting point Yt and end point e of the polygonal line together becomes a triangle indicated by L3.

The signal actually obtained, however, does not become a flat spectrum due to the unevenness of blood corpuscle density. The signal becomes the sum of spike-shaped spectral created in conformity with present corpuscles, includes various electrical noises and considerably differs from a theoretical shape due to the influence of the shape of the light receiving pupil and the influence of multiscattering, and further by the misalignment of the measuring beam and the blur of the beam by the tears in the examined eye E. Accordingly, the signal does not become a definite triangle as described above even if similar processing is conducted, and particularly the influence of multiscattering makes such a spectral shape that oozes out from the signal portion S to the white noise portion N so as to make the determination of the cut-off frequency f c difficult.

However, what corresponds to the noise portion is a white noise and therefore, pe is substantially approximate to a straight line, and if the signal is substantially good, the maximum value p exists substantially in the vicinity of the cut-off frequency fc. Further, when the obtained spectrum is approximate to a theoretical one, op linking the origin o and the maximum value p together becomes approximate to a straight line.

Figure 11:
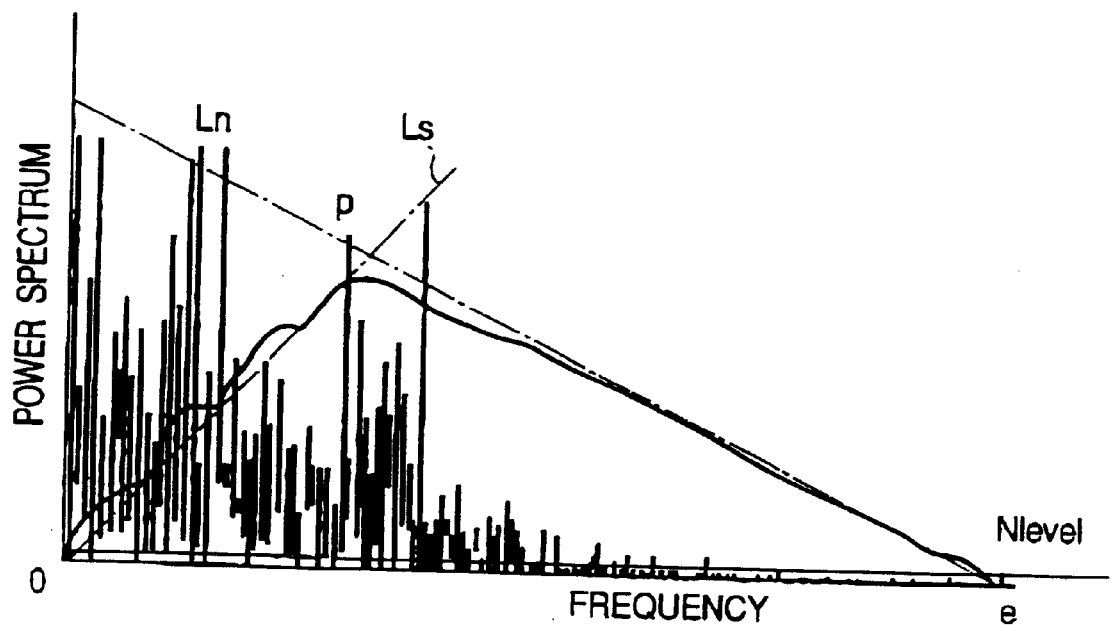
FIG. 11 is a graph of the actual shape of the light reception signal.

FIG. 11 shows the result of the application of the processing of actual FFT, and what is obtained by linking epo is a substantially triangular waveform, and Ln is a straight line in which a high frequency portion is linearly approximated, and Ls is a straight line in which a low frequency portion is linearly approximated. When the respective approximation ranges are separated, for example, at a point p, which is the maximum peak frequency of an obtained curve, the straight line Ln is from the maximum frequency to the point p, and the straight line Ls is from the origin o to the point p. At this time, regarding the approximation range of the straight line Ln, when it is taken into account that the noise is white noise, the noise portion of multiscattering can be evaluated more correctly if the approximation range is e.g., from the maximum frequency to order of p×0.8.

Here, the quality value Q, which is the indication of the quality of the signal, is calculated with the remainder between the approximately straight line Ls and the actual curve, whereby the difference between the rectangular portion of the FFT waveform theoretically calculated in the area of the signal level and the FFT waveform calculated from the output signal can be calculated and be made into a numerical value. If the design of the device is such that the result is displayed on the display 32 on the basis of this calculated value, it will become possible for the operator to judge the quality of measurement more objectively.

By once integrating the signal as described above, the influence of the void of the spectrum can be mitigated, and by calculating the point p, which is the peak frequency, the noise area and the signal area can be separated from each other relatively stable. Further, it becomes possible to make an index for effecting the discrimination of the quality of the signal by a simple calculation before the cut-off frequency fe is determined.

(b) Method of Calculating the SN ratio

When during actual measurement, for example, if the measurement of a region in which the blood flow is very slow or the blood is not at all flowing is effected, the evaluation of the obtained signal cannot be done correctly. When for example, a non-blood flow area is to be measured, theoretically the spectrum obtained ought to be only white noise. However, depending on the frequency characteristic of the circuit or the fluctuation of tracking, there is a case where a signal having some level difference is obtained. The index by the above-described quality value Q presents the quality of the signal from the shape of the spectrum, and in this case, the signal portion S may indicate a very good signal, in spite of not having sufficient intensity. In order to avoid this, the SN ratio of the obtained signal is calculated and it is used as an index for the evaluation of the reliability of blood flow velocity information.

Theoretically, the white noise portion, which is the high frequency portion of the integrated straight line L1 of the power spectrum shown in FIG. 10, is a straight line L1n, and a Y-axis segment Yn extending from the straight line L1n is indicative of the sum total of the noise portions of the obtained spectrum. Also, a Y-axis segment Yt is the sum in total of the spectrum and therefore, S=Yt−Yn can be taken as the sum total of signal components. Accordingly, the signal can be calculated by the SN ratio=S/Yt=(Yt−Yn)/Yt.

Figure 12:
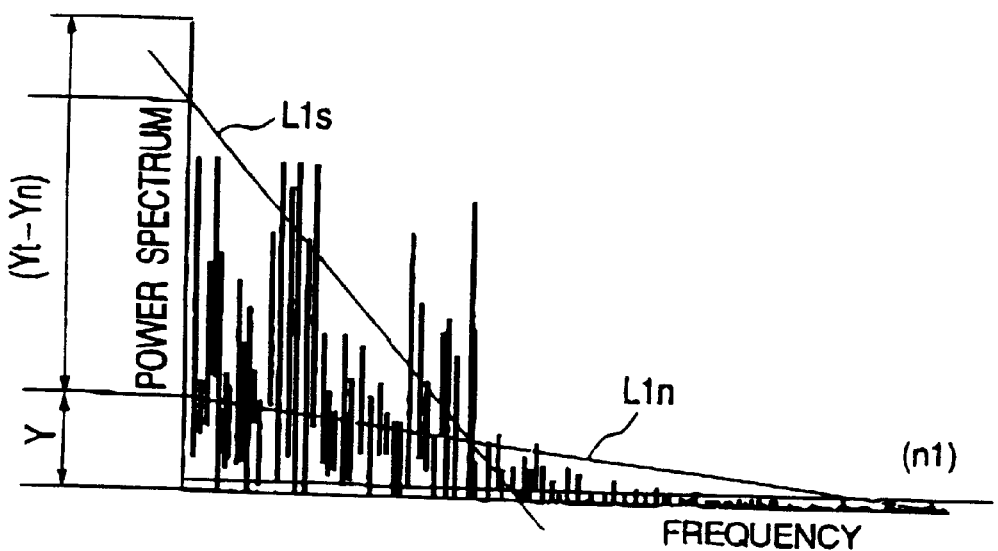
FIG. 12 is a graph of the actual shape of another light reception signal.

Actually, as shown in FIG. 12, an integrated curve is calculated, and for example, an approximate straight line L1s obtained with p×0.1 to p and for example, an approximate straight line L1n with the maximum frequency to p×0.8 or so are found, and then the Y-axis segment of the straight line L1s is defined as Yt, and the Y-axis segment of L1n is defined as Yn, whereby respective approximation ranges are found, and the SN ratio is calculated on the basis thereof. The average of the value of this SN ratio during the measuring time is found, and when the value thereof is not within an allowable range, it is regarded as a measurement error. Also, this average value may be utilized as a measure of the reliability of measurement, or may be used for judging a measurement error in which correct measurement is not effected relative to a particular time having a bad numerical value.

While in the above-described embodiment, at the step S18 of FIG. 6, the tracking reference position is set at a position at which the quality value Q becomes a minimum so that the measuring beam may irradiate this position, there is the possibility that even if the quality, value is a minimum, the value is too great and is outside the practically used range. Therefore, the design of the device may be such that the allowable range of the quality value Q is set so as to be, for example, 0<Q<Qn, and if the quality value Q is outside this range, the system controller 29 again drives the galvanometric mirror 11 so as to detect a position at which the quality value Q becomes the optimum value. In this case, for the protection of the examined eye E, when a predetermined time set by the input device 25 elapses, the system controller 29 discontinues the automatic tracking correcting operation and sets the tracking reference position to an initially set position.

Also, in order to enable the operator to more precisely choose a region to be measured, it is also possible not to set the tracking reference position to a position at which the quality value Q becomes a minimum, but to display the positions of a plurality of points at which the quality value Q is within the range of 0 to Q n and the quality value Q together, and for the system controller 29 to drive the galvanometric mirror 11 so as to move the measuring beam to any point selected from among them by the operator.

Further, when the examinee winks or greatly moves his or her eyeballs during the time when system controller 29 is driving the galvanometric mirror 11 to thereby detect the position at which the quality value Q becomes the optimum value (for example, the minimum value), a position at which the quality value Q cannot be accurately calculated may occur, or the tracking operation may become unstable and the measuring beam may greatly deviate from a measured region and may become unable to return. Therefore, a wink detecting mechanism or an eyeball motion detecting mechanism, not shown may be provided so that when the examinee's wink or great eye movement is detected, the system controller 29 may discontinue the automatic tracking correcting operation.

While in the above-described embodiment, the design is such that the SN ratio of the measurement signal obtained by t he photomultipliers 28a and 28b is calculated and if this SN ratio is within an allowable range, the quality value Q of the measurement signal is calculated and the measuring beam irradiates the position at which the quality value Q becomes a minimum value, the design may be such that both of the SN ratio and the quality value Q are normally calculated and the evaluation of the reliability of blood flow velocity information is effected with the product of the two, and the measuring beam irradiates the position which is highest in reliability.

According to the first embodiment described above, even when the measuring beam irradiates the eye at a plurality of different angles to thereby effect measurement, the measuring beam can automatically irradiate the best position of the measured vessel. Therefore, it becomes possible to always obtain a Doppler shift measuring signal of good quality accurately and simply, even for the fluctuation of the quality of the Doppler shift measuring signal from the vessel in the fundus of the eye by the indefinite elements of a living body. Also, irrespective of the operator's degree of skill, the accurate and quick measurement of the fundus-blood-flow velocity becomes possible, and the quality of the measuring signal and the measured position together are stored and displayed in a plurality, whereby the position to be measured can be precisely chosen, and by discontinuing scanning for a predetermined time, the protection of the examined eye becomes possible.

Embodiment

Figure 13:
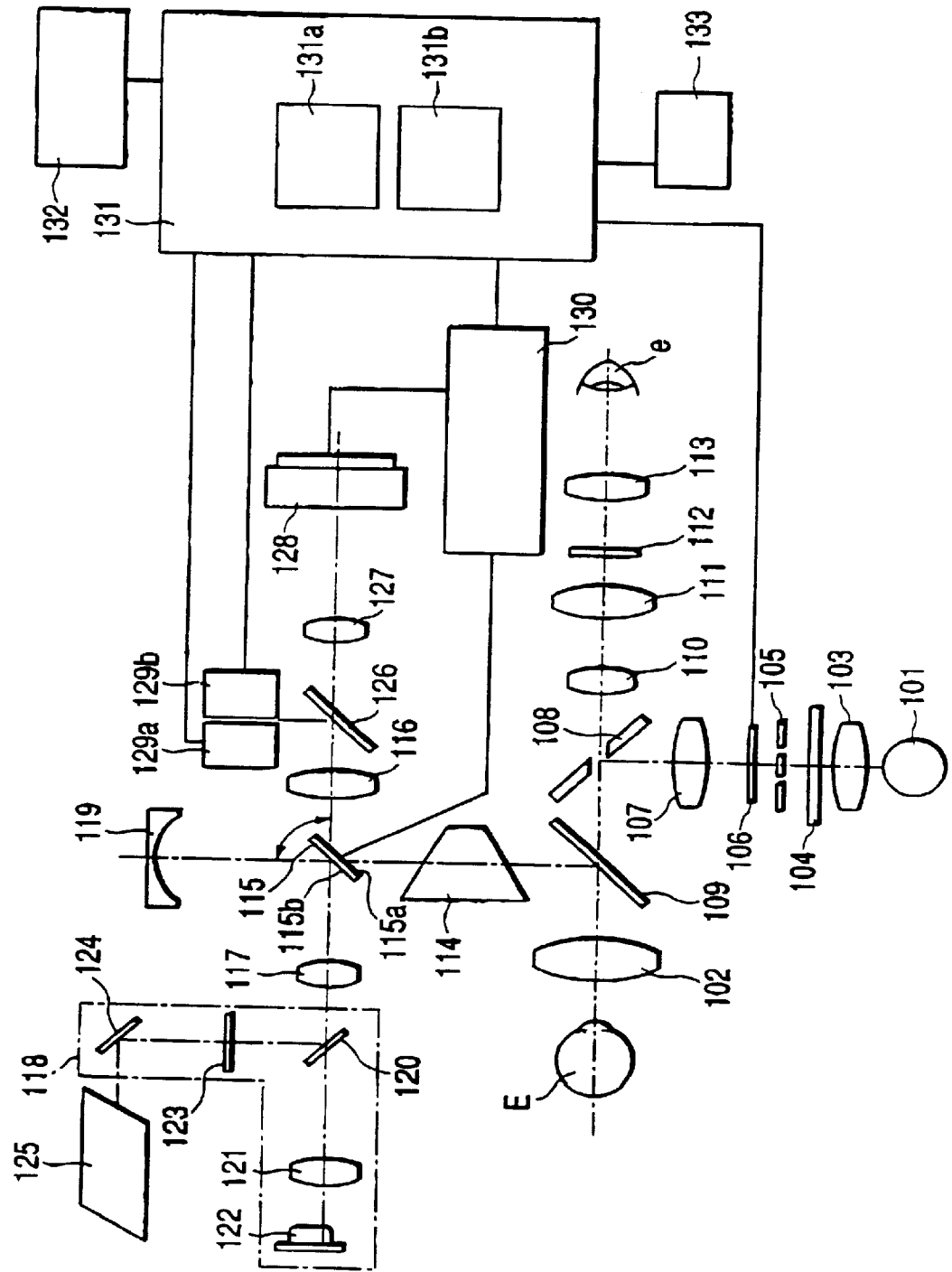
FIG. 13 shows the construction of a fundus blood flow meter according to a second embodiment of the present invention.

FIG. 13 shows the construction of a fundus-blood-flow meter according to a second embodiment of the present invention. On an illuminating optical path leading from an observation light source 101 comprising a tungsten lamp or the like emitting white light to an objective lens 102 opposed to an examined eye E, there are successively arranged a condenser lens 103, a band-pass filter 104 transmitting, for example, only a wavelength light in the yellow range therethrough, a ring slit 105 provided at a position substantially conjugate with the pupil of the examined eye E, a transmission-type liquid crystal plate 106, which is a fixed eye mark displaying element movable along the optical path, a relay lens 107, an apertured mirror 108 and a band-pass mirror 109 transmitting a wavelength light in the yellow range therethrough and reflecting almost all of the other beams, whereby a fundus illuminating optical system is constituted.

A fund us observation optical system is constructed behind the apertured mirror 108, and a focusing lens 110 movable along the optical path, a relay lens 111, a scale plate 112 and an eyepiece 113 are arranged in succession, and lead to an operator's eye e.

On the optical path in the reflecting direction of the band-pass mirror 109, there are disposed an image rotator 114 and a galvanometric mirror 115 having a rotary shaft perpendicular to the plane of the drawing sheet of FIG. 13 and having both its surfaces polished, and in the reflecting direction of the lower reflecting surface 115a of the galvanometric mirror 115, there is disposed a second focusing lens 116 movable along the optical path, and in the reflecting direction of the upper reflecting surface 115b of the galvanometric mirror 115, there are disposed a lens 117 and a focusing unit 118 movable along the optical path. The front side focal plane of the lens 117 is in conjugate relationship with the pupil of the examined eye E, and the galvanometric mirror 115 is disposed on that focal plane. Also, a concave mirror 119 is disposed rearwardly of the galvanometric mirror 115, and there is constructed a relay optical system in which a laser beam reflected by the upper reflecting surface 115b of the galvanometric mirror 115 passes through the cut-away portion of the galvanometric mirror 115.

In the focusing unit 118, a dichroic mirror 120, a condensing lens 121 and a measuring light source 22 comprising a laser diode are successively arranged on the same optical path as that of the lens 117, and on the optical path in the reflecting direction of the dichroic mirror 120, there are disposed a mask 123 and a mirror 124, and this focusing unit 118 is integrally movable in the direction of arrow. Further, on the optical path in the incidence direction of the mirror 124, there is disposed a tracking light source 25 emitting, for example, green light differing from the other light sources of high luminance.

On the optical path in the reflecting direction of the lower reflecting surface 115a of the galvanometric mirror 115, a dichroic mirror 126, a magnifying lens 127 and a one-dimensional image pickup element 128 with an image intensifier are successively arranged rearwardly of the second focusing lens 116, whereby a vessel detecting system is constituted. Also, photomultipliers 129a and 129b are disposed on the optical path in the reflecting direction of the dichroic mirror 126, whereby a light receiving optical system for measurement is constituted. For the convenience of illustration, all optical paths have been shown on the same plane, but the photomultipliers 129a and 129b are disposed in a direction orthogonal to the plane of the drawing sheet of FIG. 13.

The output of the one-dimensional image pickup element 128 is connected to a control driving circuit 130, the output of which in turn is connected to a system controller 131 for controlling the galvanometric mirror 115 and the entire apparatus. A signal processing processor 131a and a memory 131b are contained in the system controller 131, and the output of the system controller 131 is connected to the transmission-type liquid crystal plate 106 and a display 132, and the output of an operating device 133 is connected to the system controller 131.

The white light emitted from the observation light source 101 passes through the condenser lens 103, only a yellow wavelength light is transmitted through the band-pass filter 104, and the beam passing through the ring slit 105 illuminates the transmission-type liquid crystal plate 106 from the back thereof, passes through the relay lens 107, and is reflected by the apertured mirror 108. Thereafter, only the light in the yellow range is transmitted through the band-pass mirror 109, and passes through the objective lens 102 and is once imaged as a ring slit image on the pupil of the examined eye E, and thereafter substantially uniformly illuminates the fundus Ea of the eye. At this time, a fixed eye mark is displayed on the transmission-type liquid crystal plate 106, and this fixed eye mark is projected onto the fundus Ea of the examined eye E by the illuminating light, and is presented to the examinee as an eye mark image. The ring slit 105 is for separating the fundus illuminating light and the fundus observation light from each other in the front eye portion of the examined eye E, and the shape and number thereof will pose no problem if it is one forming a necessary light intercepting area.

The reflected light from the fundus Ea of the eye returns along the same optical path, is taken out as a fundus observation light beam from on the pupil, passes through the opening portion at the center of the apertured mirror 108, the focusing lens 110 and the relay lens 111, and is imaged as a fundus image Ea' by the scale plate 112, and thereafter arrives at the operator's eye e through the eyepiece 113. The operator performs the alignment of the apparatus while observing this fundus image Ea'.

A measuring beam emitted from the measuring light source 22 eccentrically passes through the upper portion of the condensing lens 121, and is transmitted through the dichroic mirror 120. On the other hand, a tracking beam emitted from the tracking light source 25 is reflected by the mirror 124, and is shaped into a desired shape by the mask 123, and thereafter is reflected by the dichroic mirror 120, and is superposed on the measuring beam being imaged in a spot shape at a position conjugate with the center of the opening portion of the mask 123 by the condensing lens 121.

Further, the measuring beam and the tracking beam pass through the lens 117, are once reflected by the upper reflecting surface 115b of the galvanometric mirror 115, and are further reflected by the concave mirror 119 and are again returned toward the galvanometric mirror 115. The galvanometric mirror 115 is disposed at a position conjugate with the pupil of the examined eye E, and the shape thereof is an asymmetrical shape on the pupil of the examined eye E. The concave mirror 119 is concentrically disposed on the optical axis, and is given the function of a relay optical system for imaging the upper reflecting surface and lower reflecting surface of the galvanometric mirror 115 at −1 time.

Therefore, the two beams reflected by the galvanometric mirror 115 are now returned to the position of the cut-away portion of the galvanometric mirror 115, and travel toward the image rotator 114 without being again reflected by the galvanometric mirror 115. The two beams deflected to the objective lens 102 by the band-pass mirror 109 via the image rotator 114 irradiate the fundus Ea of the examined eye E through the objective lens 102.

At this time, the tracking beam is shaped by the mask 123 so as to illuminate a rectangular area including a measuring point and covering the vessel thereof, and the size thereof may suitably be of the order of 300–500 $\mu$m in the vesselcular running direction and of the order of 500 to 1200 $\mu$m in a direction at a right angle with respect to the vessel. Also, the measuring beam is a circular spot having the thickness of the order of 50 to 120 $\mu$ of the vessel to be measured, or of an elliptical shape in which the vesselcular running direction is the major direction.

The scattered reflected light by the fundus Ea of the eye is again condensed by the objective lens 2, is reflected by the band-pass mirror 109, passes through the image rotator 114, is reflected by the lower reflecting surface 115a of the galvanometric mirror 115, and passes through the focusing lens 116, and the measuring beam and the tracking beam are separated from each other on the dichroic mirror 126.

The tracking beam is transmitted through the dichroic mirror 126, and is imaged on the one-dimensional image pickup element 128 as a vesselcular image Ev' more magnified than the fundus image Ea' by the fundus observation optical system, by the magnifying lens 127, and the image pickup range at this time is substantially of the same size as the application range of the tracking beam. This vesselcular image signal is inputted to the control driving circuit 130, and is converted into a position signal of the vessel Ev. The control driving circuit 130 controls the rotation angle of the galvanometric mirror 115 by the use of this signal, and effects the tracking of the vessel Ev.

Also, part of the scattered reflected light on the fundus Ea of the eye by the measuring beam and the tracking beam is transmitted through the band-pass mirror 109, and is directed to the fundus observation optical system behind the apertured mirror 108, and the tracking beam is imaged as a bar-shaped indicator on the scale plate 112, and the measuring beam is imaged as a spot image on the central portion of this indicator. These images are observed with the fundus image Ea' and the eye mark image by the operator through the eyepiece 113. At this time, the spot image of the measuring beam is superposed on the center of the indicator, and the indicator can be one-dimensionally moved on the fundus Ea of the eye by the galvanometric mirror 115 being rotated by the operating device 133.

In case of measurement, the operator first performs the focusing of the fundus image Ea'. When the focusing knob of the operating device 133 is adjusted, the transmission-type liquid crystal plate 106, the focusing lenses 110, 116 and the focusing unit 118 are moved along the optical path in operative association with one another by a driving mechanism, not shown. When the fundus image Ea' is focused, the transmission-type liquid crystal plate 106, the scale plate 112, and the one-dimensional image pickup element 128 become conjugate with the fundus Ea of the image at a time.

In an actual examination, the operator focuses the fundus image Ea', and thereafter induces the line of sight of the examined eye E, changes the observation area, and operates the operating device 133 to move the vessel Ev to be measured to a suitable position. The system controller 131 controls the transmission type liquid crystal plate 106 and moves the eye mark image, and the image rotator 114 is rotated and operated so that a line linking the centers of the photomultipliers 129a and 129b together may become parallel to the running direction of the vessel Ev to be measured. At this time, the galvanometric mirror 115 is rotated, whereby the direction of the pixel arrangement of the one-dimensional image pickup element 128 and the direction of the moving measuring beam are adjusted to directions perpendicular to the vessel Ev at a right angle with respect thereto.

Figure 14:
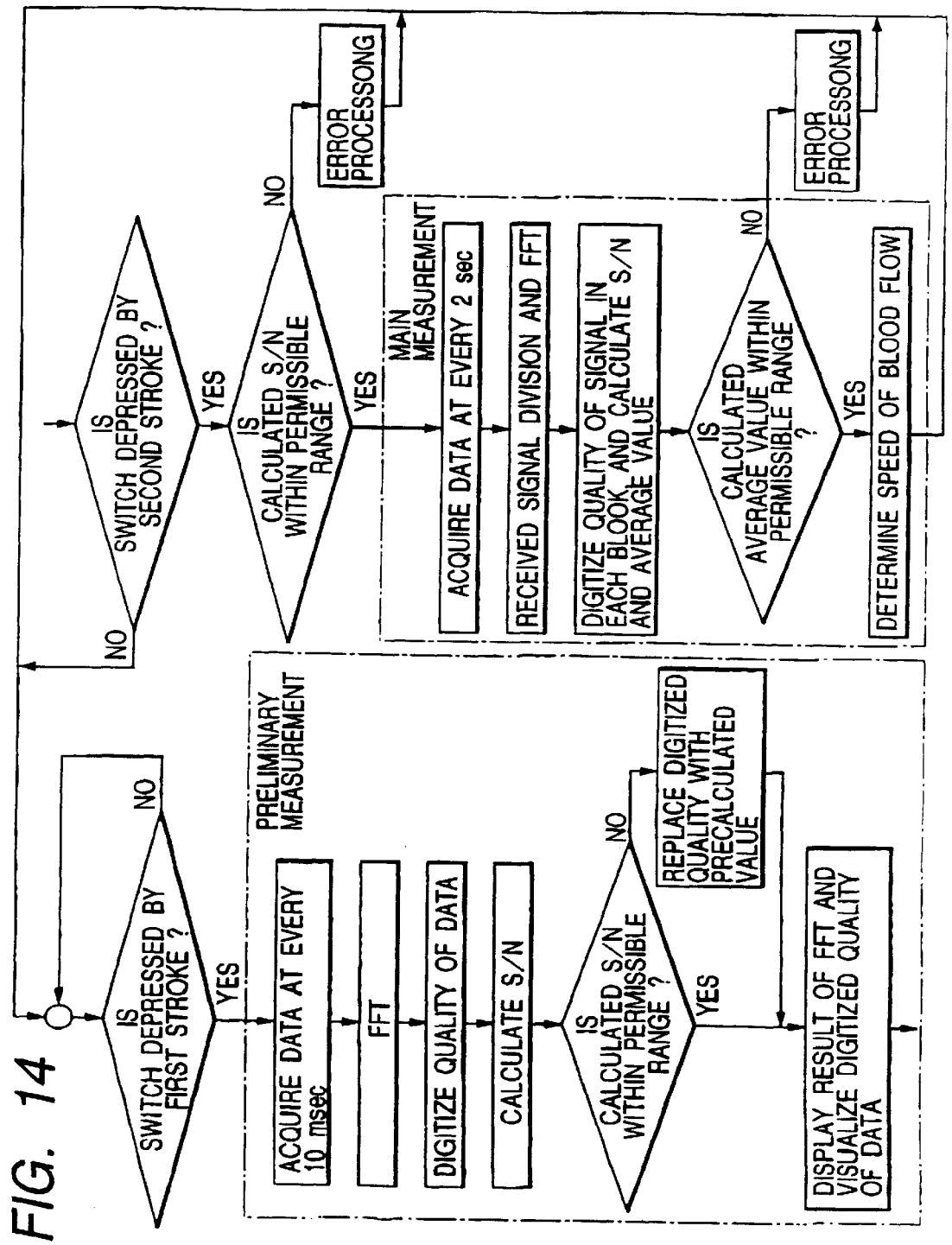
FIG. 14 is a flow chart of the operation and signal processing of the present invention.

FIG. 14 shows a flow chart of the measuring operation. The operator first depresses the measuring switch of the operating device 33 by a stroke to thereby start preliminary measurement. At this time, the state of tracking and the quality of the obtained signal are confirmed, whereafter the measuring switch is depressed by a second stroke to thereby start main measurement. In the meantime, the measuring beam is held on the vessel Ev by the work of a vesselcular tracking system, but the scattered reflected light thereof is reflected by the dichroic mirror 126 and is received by the photomultipliers 129a and 129b. The outputs of the photomultipliers 129a and 129b are put out to the system controller 131, and are stored in the memory 131b, and thereafter are converted into data representing blood flow velocity via such processing as frequency analysis by the signal processing processor 131a.

Figure 15:
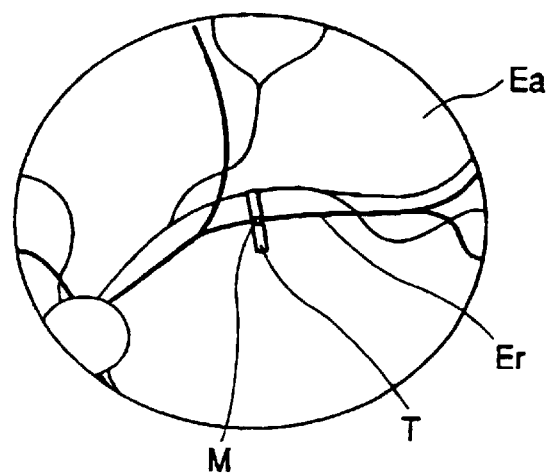
FIG. 15 is an illustration of an observed fundus image.
Figure 16:
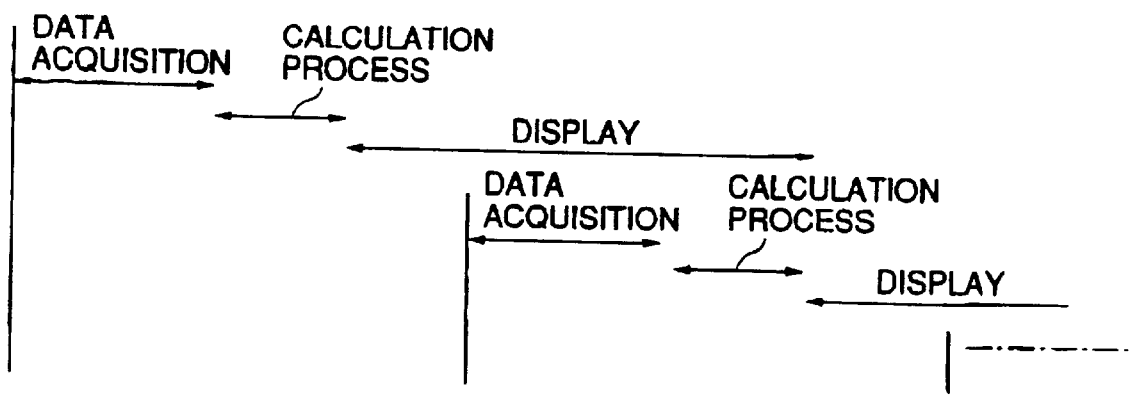
FIG. 16 is a timing chart of a processing signal.

FIG. 15 shows the state of the fundus Ea of the eye at that time, and the measuring beam M and the tracking beam T irradiate the measured vessel Ev on the fundus Ea of the eye. The signals received by the two photomultipliers 129a and 129b are intermittently A/D-converted every 10 msec. each as shown, for example, in the flow timing chart of FIG. 16, and are introduced into the memory 131b of the system controller 131, and in the signal processing processor 131a, frequency analysis (FFT processing) is first effected on the respective output signals, whereafter the difference from the theoretically found FFT signal is rendered into a numerical value. The degree of the quality of this signal rendered into a numerical value is converted, for example, into a shape easy to be visually judged, like a bar graph, and is displayed on the display 132 with the waveform of the result of FET. As a result, it becomes possible for even an inexperienced operator to grasp in a moment the difference from the theoretical FFT signal that is difficult to grasp unless sufficiently experienced, by looking at the shape of the FFT.

It is usual that the analyzing method shown herein is actually incorporated into the apparatus as software. This software is supplied by an extraneous medium such as a floppy disc or CDROM, and is installed in the main body before it is used. However, when for example, analysis only is to be effected by a discrete apparatus such as an ordinary personal computer, it is also possible by installing this software in the discrete apparatus, and in this case, it is not necessary to have an optical system or the like for measuring.

In the preliminary measurement, the above-described operation is repetitively performed, and the operator looks at the FFT waveform or the bar graph displayed at real time on the display 132 to thereby set a condition and a region for which correct measurement is possible in the main measurement. For example, when there is the deviation of the measuring beam caused by the astigmatism of the examined eye E, the operator turns a dial, not shown, provided on the operating device 133 so that the measuring beam M may irradiate the vessel while looking at the display on the display 132, whereupon the system controller 131 gives a shift amount to the galvanometric mirror 115 through the control driving circuit 130, and moves the irradiated position of the measuring beam M relative to the vessel being subjected to tracking.

As the irradiated position of the measuring beam M moves, the FFT waveform and bar display displayed on the display 132 change, and the best state is displayed when the measuring beam M has come to such a position that includes the center of the vessel which is at the maximum blood flow velocity and that does not include the other portions than the vessel as far as possible. Here, the operator again depresses the measuring switch to thereby start main measurement. When the main measurement is started, the system controller 131 stores in the memory 131b the continuous output signals from the photomultipliers 129a and 129b corresponding to a predetermined time such as 2 seconds. The stored output signals are FFT-converted by the process processing processor 131a after the measurement, and maximum Doppler shift amounts Δfmax1 and Δfmax2 are found and the maximum blood flow velocity is calculated.

Figure 17:
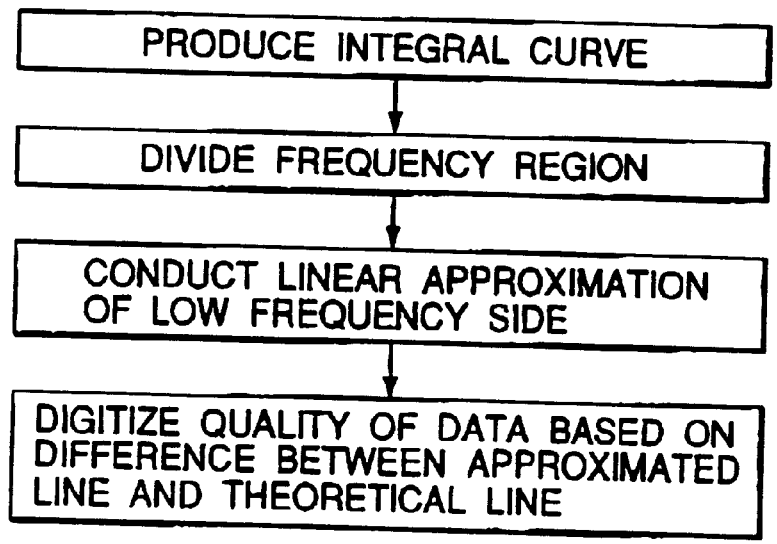
FIG. 17 is a flow chart of the digitization of the quality of a signal.
Figure 18:
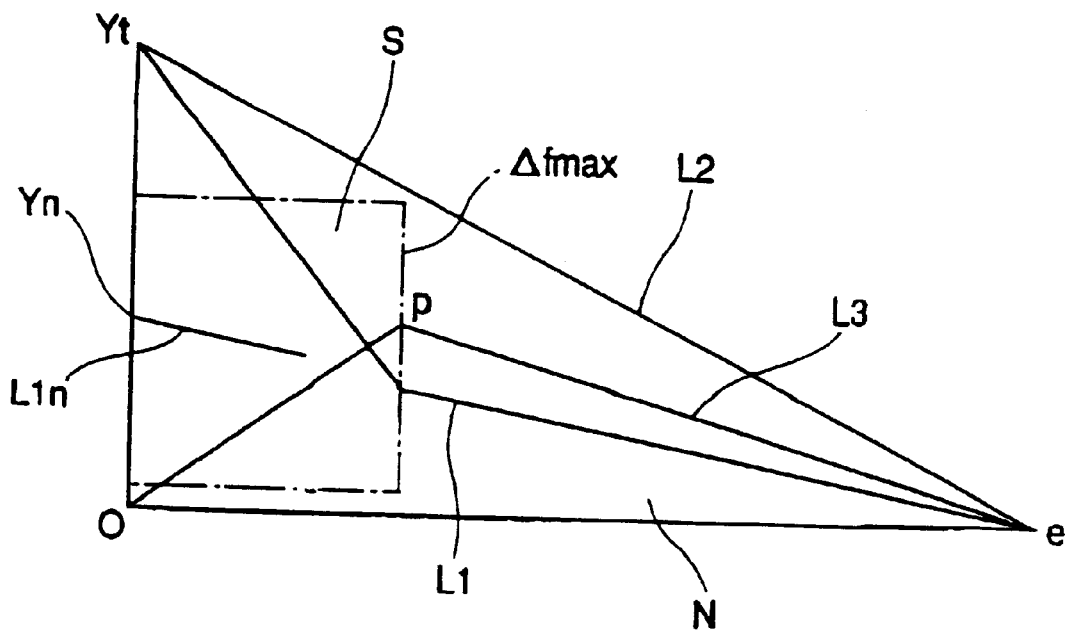
FIG. 18 is a graph of the theoretical shape of a light reception signal.

FIG. 17 shows a flow chart for quantifying the difference between the shape of FFT in the above-described operation and the theoretically found FFT signal. When the size of the light receiving pupil is neglected, the shape of the theoretically found FFT graph becomes step-like as shown in FIG. 18, and can be divided into a signal portion S indicative of a Doppler shift and a white noise portion N on the high frequency side. When this waveform is integrated from the high frequency side, a polygonal line indicated by L1 is obtained, and a value obtained by subtracting L1 from a straight line L2 linking the starting point and the end point thereof together becomes a triangle indicated by ope.

The actually obtained signal does not become a flat spectrum due to the unevenness of the blood corpuscle density. The signal becomes the sum of spike-shaped spectra created in conformity with existing corpuscles, includes various electrical noises and considerably differs from a theoretical shape due to the influence of the shape of the light receiving pupil, the influence of multiscattering, and further the misalignment of the measuring beam and the blur of the beam by the tears in the examined eye B. Accordingly, even if similar processing is effected, the signal does not become such a clear triangle, but particularly the influence of multiscattering makes such a spectral shape that oozes out from the signal portion S to the white noise portion N, and makes the determination of the cut-off frequency fc difficult.

However, what corresponds to the noise portion is white noise and therefore, pe is substantially approximate to a straight line, and if the signal is substantially good, the maximum value p exists substantially in the vicinity of the cut-off frequency fc. Further, when the obtained spectrum is approximated to the theoretical one, op also becomes approximate to a straight line.

Figure 19:
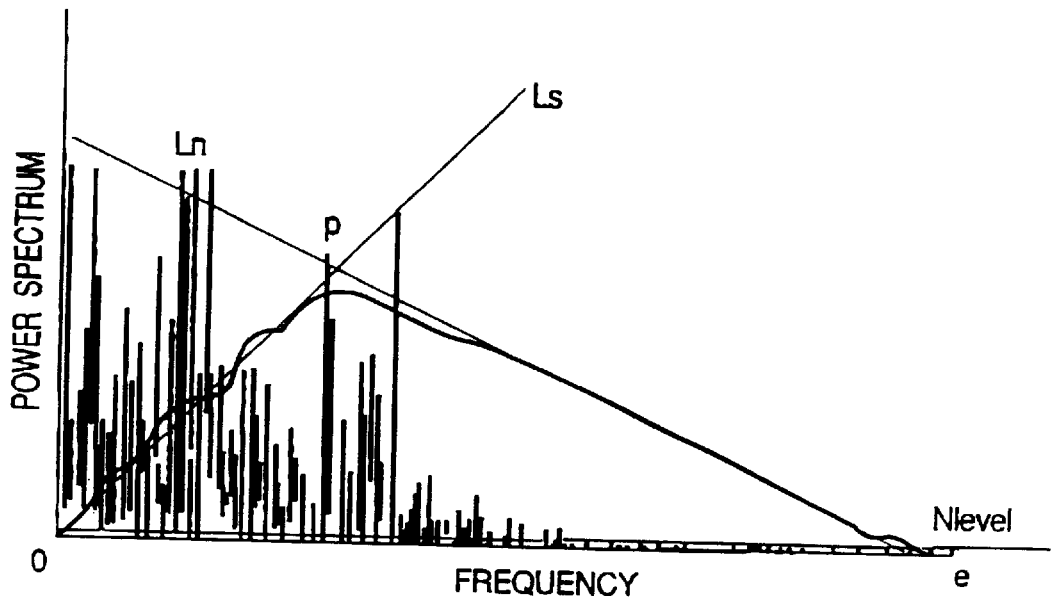
FIG. 19 is a graph of the actual shape of the light reception signal.

FIG. 19 shows the result of the application of the actual processing of FFT, and the result is a substantially triangular waveform obtained by linking epo, and Ln is a straight line in which the high frequency portion has been rectilinearly approximated, and Ls is a straight line in which the low frequency portion has been linearly approximated. When the respective approximation ranges are separated, for example, at a point p, which is the maximum peak frequency of an obtained curve, the straight line Ln is from the maximum frequency to the point p, and the straight line Ls is from the point o to the point p. At this time, as regards the approximation range of the straight line Ls, it is greatly affected by the state of tracking or eyelashes or the like and therefore, it is to be understood that the lowest frequency portion is e.g. from p×0.1 to p. Also, as regards the approximation range of the straight line Ln, when it is taken into account, that the noise is white noise, the noise portion of multiscattering can be evaluated more correctly if it is, for example, from the maximum frequency to the order of p×0.8.

Here, the index which provides the judgment of the quality of the signal is calculated by the remainder between the approximately straight line Ls and the actual curve, whereby the difference between the rectangular portion of the FFT waveform theoretically calculated in the area of the signal level and the FFT waveform calculated from the output signal can be calculated and rendered into a numerical value. If the design of the device is made such that this numerical value is displayed on the screen of the display 132, it will become possible for the operator to, judge the quality of measurement more objectively.

Figure 20A:
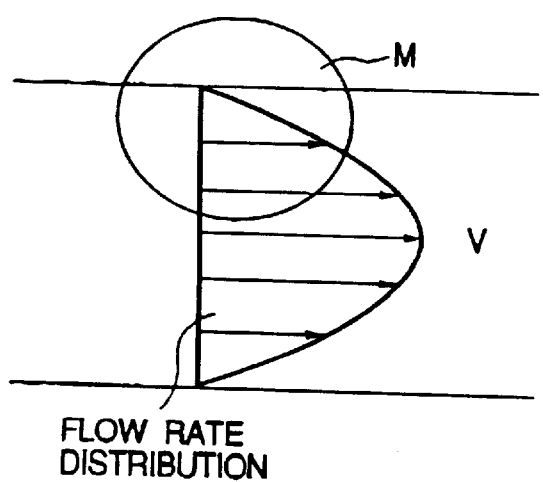
FIGS. 20A and 20B are graphs of the signal change when a measuring beam deviates from a vessel.

On the other hand, if the alignment is bad or there is great corneal astigmatism or the like in the examined eye E, positional deviation will occur between the tracking center of the tracking beam T and the measuring beam M. When as shown in FIG. 20A, the measuring beam M irradiates the vessel Ev with a deviation relative thereto, even if tracking is accurately effected on the vessel Ev, the signal light from the maximum blood flow velocity becomes null and the reflected light irregularly scattered by the retina other than the vessel gets mixed in the signal light from the vessel Ev because the measuring bean M does not irradiate the center of the vessel Ev.

Figure 20B:
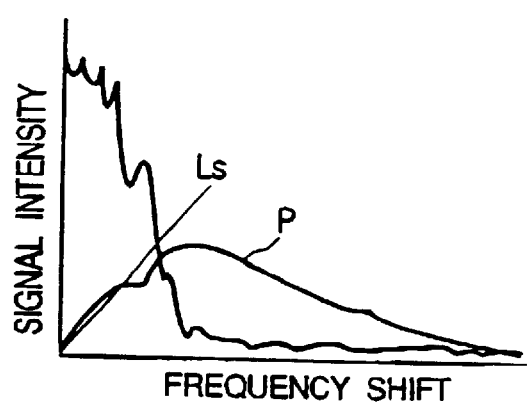
Figure 21A:
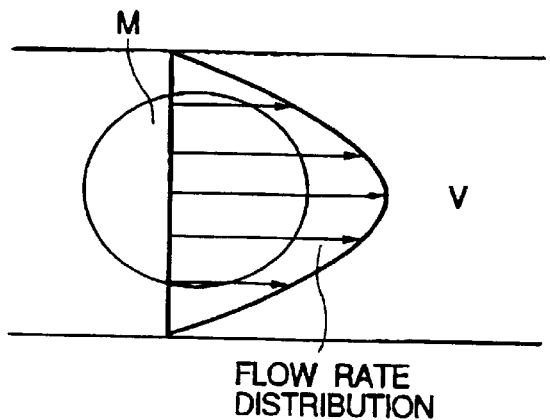
FIGS. 21A and 21B are graphs of the signal change when the measuring beam irradiates the vessel.
Figure 21B:
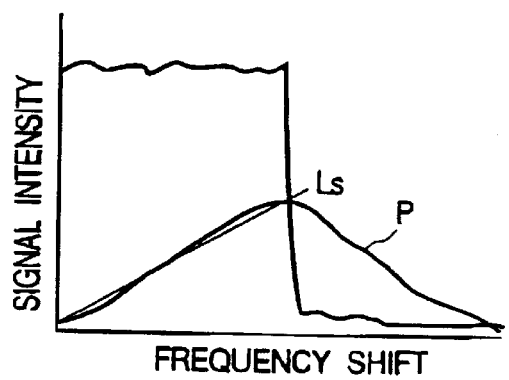

Therefore, the FFT waveform calculated by the signal processing portion 3la in response to the output signals from the photomultipliers 129a and 129b becomes a suddenly falling waveform as shown in FIG. 21B when as shown in FIG. 21A, the measuring beam M irradiates the center of the vessel Ev, whereas if the other case occurs, it becomes a waveform smoothly connected from a Doppler-shifted area to a noise level as shown in FIG. 20B. Accordingly, the low frequency portion of a calculated substantially triangular curve has a great remainder with respect to the approximately straight line thereof and therefore, it is rendered into a numerical value that the degree of the quality of the signal is bad. The operator can judge by looking at the visualized bar graph of this numerical value or the FFT waveform, that a correct result cannot be obtained even if main measurement is directly effected and the blood flow velocity is found.

When in actual measurement, for example, the measurement of a region in which the blood flow is very slow or no blood is flowing is effected, the evaluation of an obtained signal cannot be done correctly. When for example, a non-blood flow area is measured, theoretically an obtained spectrum ought to be white noise alone. However, depending on the frequency characteristic of the circuit or the fluctuation of tracking, there exists a case where a signal having some level difference is obtained. The above-described index judges the quality of the signal from the shape of the spectrum, and in this case, the signal portion S may show a very good signal in spite of not having sufficient intensity. To avoid this, the SN ratio of the obtained signal is calculated and this is used as an index for the evaluation of the reliability of blood flow velocity information.

Figure 22:
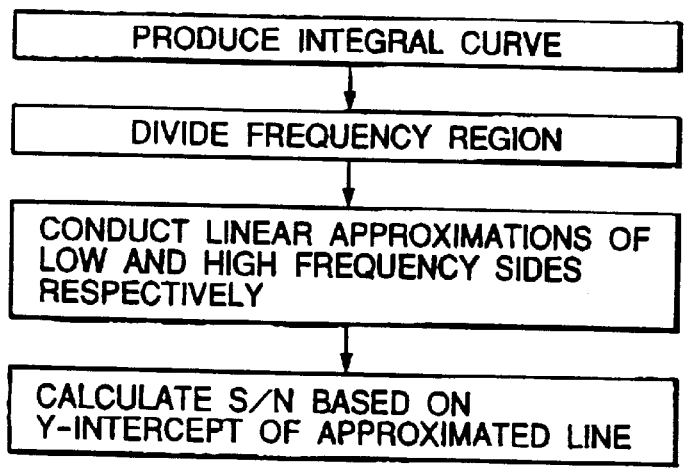
FIG. 22 is a flow chart of the calculation of the SN ratio.

FIG. 22 shows a flow chart for calculating the SN ratio. Theoretically, a white noise portion N, which is the high frequency portion of the integrated straight line, L1 of the spectrum shown in FIG. 18, is a straight line L1n, and a Y-axis segment Yn extending from the straight line L1n is indicative of the sum total of the noise portions of the obtained spectrum. Also, since the Y-axis segment Yt of the straight line L1 is the sum total of spectrum, S=Yt−Yn can be taken as the sum total of signal components. Accordingly, the signal can be calculated by the SN ratio=S/Yt=(Yt−Yn)/Yt.

Figure 23:
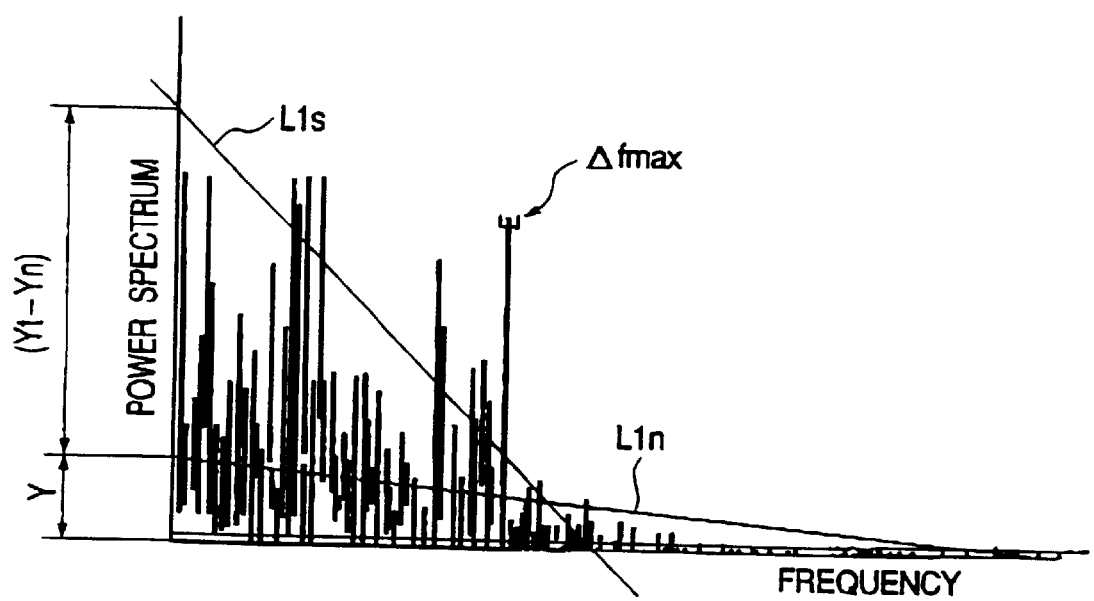
FIG. 23 is a graph of the actual shape of a light reception signal.

Actually, as shown in FIG. 23, an integrated wave is calculated. For example, an approximately straight line L1S obtained from p×0.1 to p and for example, an approximately straight line L1n, obtained from a maximum frequency to the order of p×0.8, are found, and then the Y-axis segment of the straight line L1s is defined as Yt and the Y-axis segment of the straight line L1n is defined as Yn, whereby the respective approximation ranges are found, and the S/N ratio is calculated on the basis thereof.

It is usual that the analyzing method shown herein is actually incorporated into the apparatus as software. This software is supplied by an extraneous medium such as a floppy disc or CDROM, and is installed in the main body before it is used. However, when for example, it is desired to effect analysis only by a discrete apparatus such as an ordinary personal computer, it is also possible to install this software in the discrete apparatus, and in this case, it is not necessary to have an optical system or the like for measurement.

In the preliminary measurement by the flow chart of FIG. 14, the quality of the signal is rendered into a numerical value, whereafter the SN ratio is calculated, and when the SN ratio is outside the range of an allowable value, an optimum value is substituted for the numerical value. By performing the above-described operation, when the SN ratio is bad, that is, when measurement becomes bad, it can be prevented from being mistaken for a good signal. Also, in the main measurement of FIG. 14, when the SN ratio is bad at a point of time at which the measurement has been started, the main measurement is regarded as wrong and an error display is effected to thereby cancel useless measurement. Further, when the average of the S/N ratios during the measuring time is taken and the value thereof is not within all allowable range, the measurement may be regarded as an error, or may be used for the judgment of an error that correct measurement has not been effected, to a particular time having a bad numerical value.

Also, if design of the device is such that the system controller 131 compares a preset allowable value and a calculated value with each other and effects the control of outputting a measurement starting input signal for shifting to the main measurement when the calculated value becomes less than the allowable value, the operator's trouble can be saved. Further, the output signals from the two photomultipliers 129a and 129b are processed during the preliminary measurement, but the two photomultipliers 129a and 129b only differ in the light receiving direction relative to a measured region and therefore, if the light receiving situation of one photomultiplier 29a is known, the light receiving situation of the other photomultiplier 29b can be substantially foreseen. Accordingly, in order to reduce the burden of the signal processing portion 31 and shorten the processing time, the design of the device may be such that signal processing is effected on only the output signal from one photomultiplier 29a and displayed.

While in the above-described embodiment, there has been shown a method of utilizing the SN ratio separately from the numerical value for judging the degree of the quality of the previous signal, the SN ratio may be added to this numerical value and a new standard for judging the quality of the signal may be prepared, and the average value of this numerical value during the measuring time can also be utilized as the reliability of measurement According to the second embodiment described above, when the SN ratio of the Doppler signal is to be calculated, it is once integration-processed to thereby mitigate the influence of the void of the spectrum. Also, the peak frequency can be calculated to thereby separate the noise area and the signal area from each other relatively stably. Also, before the cut-off frequency is determined, an index for effecting the calculation of the SN ratio and the judgment of the quality of the signal by simple calculation can be made. Also, if processing is carried out in the preliminary measurement, the operator can correctly judge whether the measurement in the main measurement is good or not, by looking at the FFT waveform or the bar graph displayed on the display at real time, and therefore the load to the examinee can be decreased and at the same time, the measuring time can be shortened.

Also, there are various available methods such as not only the calculation of the S/N ratio of a signal but also velocity analysis by separating a certain frequency area and the white noise area of the signal from each other. When use is made of the difference from the FFT signal theoretically found in the actual velocity calculation, it is also possible to use the level of white noise found by the present method for the determination of the shape of the theoretical FFT signal. Thereby, the conformability between the theoretical shape and the actually obtained signal can be enhanced and velocity calculation conforming to practice becomes possible.

What is claimed is:

1. A fundus examination apparatus comprising:

an irradiating system configured to irradiate the fundus of an examined eye with a measuring beam, said irradiating system including a deflector configured to deflect the measuring beam and change the position of the measuring beam on the fundus;

a light receiving system configured to receive the scattered light from the fundus of the eye by said measuring beam, and to obtain a signal of the scattered light of the measuring beam necessary for examination;

a tracking system configured to irradiate the fundus of the eye with a tracking beam, wherein said light receiving system is configured to receive a scattered tracking beam scattered from the fundus of the eye and to produce an image signal of a region illuminated by the tracking beam, wherein said tracking system is configured to control said deflector on the basis of the image signal of the region illuminated by said tracking beam; and a controller having a processor configured to evaluate the signal of the scattered light of the measuring beam obtained by said light receiving system, and to control said deflector on the basis of the image signal and the evaluation result during the execution of tracking to thereby correct the irradiated position of said measuring beam.

2. A fundus examination apparatus according to claim 1, further comprising a memory for storing therein the moved position of said measuring beam and the result of said evaluation corresponding to said moved position, and a display for displaying the result of said evaluation.

3. A fundus examination apparatus according to claim 1, further comprising setting means for setting the range of movement, and wherein said controller moves the irradiated position of said measuring beam within said range.

4. A fundus examination apparatus according to claim 1, wherein said controller includes a memory for storing the movement starting position of the irradiated position of said measuring beam therein, and refers to said memory to thereby enable the irradiated position of said measuring beam to be returned to said movement starting position at any time during the movement of the irradiated position of said measuring beam.

5. A fundus examination apparatus according to claim 1, wherein the measuring beam is Doppler-shifted when the measuring beam irradiates the fundus of the examined eye to produce Doppler-shifted scattered light, wherein said processor is configured to evaluate the signal necessary for examination obtained by said light receiving system, wherein said processor has a processor configured to frequency-analyze the Doppler-shifted scattered light, and to calculate the velocity of blood flow in a vessel on the fundus of the eye.

6. A fundus examination apparatus comprising:
an irradiating system configured to irradiate the fundus of an examined eye with a measuring beam, said irradiating system including a deflector configured to deflect the measuring beam and change the position of the measuring beam on the fundus;
a light receiving system configured to receive the scattered light from the fundus of the eye by said measuring beam, and to obtain a signal of the scattered light of the measuring beam necessary for examination;
a tracking system configured to irradiate the fundus of the eye with a tracking beam, wherein said light receiving system is configured to receive a scattered tracking beam scattered from the fundus of the eye and to produce an image signal of a region illuminated by the tracking beam, wherein said tracking system is configured to control said deflector on the basis of the image signal of the region illuminated by said tracking beam; and
a controller having a processor configured to evaluate the signal of the scattered light of the measuring beam obtained by said light receiving system, and to control said deflector on the basis thereof during the execution of tracking to thereby correct the irradiated position of said measuring beam, wherein said processor is configured to find the reliability of the signal necessary for examination by performing a process including the calculation of the signal-to-noise ratio of the light necessary for examination and wherein said processor is also configured to effect said evaluation.

7. A fundus examination apparatus according to claim 6, wherein said processor is configured to calculate a quality value when said calculated signal-to-noise ratio is within an allowable range, and said controller is configured to change a reference position of tracking on the basis of said quality value.

8. A fundus examination apparatus according to claim 7, wherein said processor finds a position at which said quality value becomes optimum, and said controller changes the reference position of tracking so that said measuring beam irradiates said position.

9. A fundus examination apparatus according to claim 6, wherein said processor calculates a quality value together with said signal-to-noise ratio, and effects the evaluation of said reliability by the product of the two.

10. A fundus examination apparatus according to claim 6, wherein said processor executes signal processing including a first step of calculating an integrated curve in which the spectral distribution of a result of frequency analysis of said signal necessary for examination is accumulated from a high frequency side, a second step of dividing said spectral distribution into at least two frequency areas which are a noise area existing in a high frequency area and approximated to white noise, and a signal area existing more adjacent to a low frequency side than said noise area, by the use of said integrated curve, a third step of linearly approximating the integrated curve in said two divided frequency areas, and a fourth step of calculating the signal-to-noise ratio of said signal necessary for examination on the basis of two approximately straight lines obtained at said third step.

11. A fundus examination apparatus comprising:
an irradiating system for irradiating the fundus of an examined eye with a measuring beam;
a light receiving system for receiving the scattered light from the fundus of the eye by said measuring beam, and obtaining a signal necessary for examination; and
a processor for frequency-analyzing the signal obtained by said light receiving system, and calculating the velocity of blood flow in a vessel on the fundus of the eye,
said processor executing signal processing including a first step of calculating an integrated curve in which the spectral distribution of the result of said frequency analysis is accumulated from a high frequency side, and a second step of dividing said spectral distribution into at least two areas which area noise area existing in a high frequency area and approximated to white noise, and a signal area existing more adjacent to a low frequency side than said noise area, by the use of said integrated curve.

12. A fundus examination apparatus according to claim 11, wherein said processor executes signal processing further including a third step of linearly approximately the integrated curve in said two divided frequency areas, and a fourth step of calculating the signal-to-noise ratio of said signal necessary for examination on the basis of two approximately straight lines obtained at said third step.

13. A fundus examination apparatus according to claim 11 or 12, wherein at said second step, said areas are divided on the basis of a frequency at which the distance between said integrated curve and a straight line linking the starting point and end point of said integrated curve together becomes maximum.

14. A fundus examination apparatus according to claim 12, further comprising a controller for effecting control of said apparatus on the basis of the signal-to-noise ratio calculated by said processor so as to regard examination as an error or cancel examination.

15. A fundus examination apparatus according to claim 14, wherein said controller preliminarily receives the signal necessary for examination prior to actual measurement, and effects control of said apparatus so as to cancel examination when the signal-to-noise ratio of said preliminary received signal is not within an allowable range.

16. A method of measuring flow velocity comprising the steps of:
irradiating an examined portion with a measuring beam through a deflector, and detecting the scattered light from said examined portion by a detecting system;

irradiating the vicinity of the examined portion with a tracking beam through said deflector to thereby obtain tracking information, and controlling said deflector on the basis of the tracking information and executing tracking;

calculating a position at which the reliability of detected signals of said detecting system is relatively improved during the tracking using at least the signal-to-noise ratio of the detected signals, and controlling said deflector so that said measuring beam irradiates said position; and frequency-analyzing the detected signals obtained by said detecting system and calculating the flow velocity of a fluid flow through the examined portion.

* * * * *

UNITED STATES PATENT AND TRADEMARK OFFICE
CERTIFICATE OF CORRECTION

PATENT NO. : 6,332,683 B1
DATED : December 25, 2001
INVENTOR(S) : Shigeaki Ono et al.

It is certified that error appears in the above-identified patent and that said Letters Patent is hereby corrected as shown below:

Drawings,
Sheet No. 10, Figure 14, "PROCESSONG" (both occurrences) should read
-- PROCESSING --.

Column 2,
Line 47, "luent" should read -- ment --.
Line 50, "metry" should read -- metry: --.

Column 3,
Line 16, "specific-" should read -- specific --.

Column 4,
Line 64, "Embodiment" should read -- Embodiment 1 --.

Column 5,
Line 42, "20' " should read -- 20 --.

Column 9,
Line 27, "Da +," should read -- Da + $\propto$, --.

Column 10,
Line 5, "in" should be deleted.
Line 6, "coincident" should read -- incoincident --.
Line 63, "f c" should read -- fc --.

Column 11,
Line 38, "fe" should read -- fc --.

Column 12,
Line 36, "Q n" should read -- Qn --.

UNITED STATES PATENT AND TRADEMARK OFFICE
CERTIFICATE OF CORRECTION

PATENT NO.   : 6,332,683 B1
DATED        : December 25, 2001
INVENTOR(S)  : Shigeaki Ono et al.

It is certified that error appears in the above-identified patent and that said Letters Patent is hereby corrected as shown below:

Column 13,
Line 17, "Embodiment" should read -- Embodiment 2 --.
Line 35, "fund us" should read -- fundus --.

Column 15,
Line 28, "120 $\mu$ of" should read -- 120 $\mu$ of --.

Column 18,
Line 26, "to," should read -- to --.

Signed and Sealed this

Fourth Day of February, 2003

JAMES E. ROGAN
*Director of the United States Patent and Trademark Office*